(12) United States Patent
Williams

(10) Patent No.: US 9,364,220 B2
(45) Date of Patent: Jun. 14, 2016

(54) APPARATUS FOR ENDOSCOPIC PROCEDURES

(71) Applicant: Covidien LP, Mansfield, MA (US)

(72) Inventor: Justin Williams, Naugatuck, CT (US)

(73) Assignee: Covidien LP, Mansfield, MA (US)

( * ) Notice: Subject to any disclaimer, the term of this patent is extended or adjusted under 35 U.S.C. 154(b) by 568 days.

(21) Appl. No.: 13/864,771

(22) Filed: Apr. 17, 2013

(65) Prior Publication Data

US 2013/0334281 A1 Dec. 19, 2013

Related U.S. Application Data

(60) Provisional application No. 61/661,461, filed on Jun. 19, 2012.

(51) Int. Cl.
*A61B 17/068* (2006.01)
*A61B 17/072* (2006.01)
(Continued)

(52) U.S. Cl.
CPC ......... *A61B 17/068* (2013.01); *A61B 17/07207* (2013.01); *A61B 17/07292* (2013.01); *A61B 2017/0038* (2013.01); *A61B 2017/0046* (2013.01); *A61B 2017/00314* (2013.01); *A61B 2017/00327* (2013.01);
(Continued)

(58) Field of Classification Search
CPC ........... A61B 17/068; A61B 17/07207; A61B 2017/00353; A61B 2017/00367; A61B 2017/00398; A61B 2017/2903; A61B 2017/2932; A61B 17/0038; A61B 17/00353
USPC ............... 227/176.1, 175.1, 19, 178.1, 180.1, 227/175.2; 606/139, 153, 219
See application file for complete search history.

(56) References Cited

U.S. PATENT DOCUMENTS 2,777,340 A 1/1957 Hettwer et al.
2,957,353 A 10/1960 Babacz
(Continued)

FOREIGN PATENT DOCUMENTS

AU 2008229795 A1 4/2009
CA 2451558 A1 1/2003
(Continued)

OTHER PUBLICATIONS

European search Report from Appl. No. 13177163.6 dated Nov. 15, 2013. (8 pp).
(Continued)

*Primary Examiner* — Hemant M Desai
*Assistant Examiner* — Lucas Palmer

(57) ABSTRACT

The present disclosure relates to electromechanical surgical systems configured for use with removable disposable loading units and/or single use loading units for clamping, cutting and/or stapling tissue. A force transmitting assembly of surgical instrument transmits a rotation of a rotatable drive member of the surgical instrument to the rotation receiving member of the end effector. A distal neck assembly of the surgical instrument includes at least one gear system configured to convert a rotational input of the rotatable drive member into at least two output forces to the end effector; and an articulating neck assembly interconnecting the tubular body and the distal neck housing. The articulating neck assembly is configured to enable off-axis articulation of the distal neck assembly. The rotatable drive member extends through the articulating neck assembly.

26 Claims, 23 Drawing Sheets

(51) Int. Cl.
  *A61B 17/00* (2006.01)
  *A61B 17/29* (2006.01)
(52) U.S. Cl.
  CPC ........... *A61B 2017/00367* (2013.01); *A61B 2017/00398* (2013.01); *A61B 2017/00477* (2013.01); *A61B 2017/00734* (2013.01); *A61B 2017/07278* (2013.01); *A61B 2017/2903* (2013.01); *A61B 2017/2905* (2013.01); *A61B 2017/2908* (2013.01); *A61B 2017/2925* (2013.01); *A61B 2017/2927* (2013.01); *A61B 2017/2929* (2013.01); *A61B 2017/2931* (2013.01)

(56) References Cited

U.S. PATENT DOCUMENTS

| | | | |
|---|---|---|---|
| 3,111,328 | A | 11/1963 | Di Rito et al. |
| 3,695,058 | A | 10/1972 | Keith, Jr. |
| 3,734,515 | A | 5/1973 | Dudek |
| 3,759,336 | A | 9/1973 | Marcovitz et al. |
| 4,162,399 | A | 7/1979 | Hudson |
| 4,606,343 | A | 8/1986 | Conta et al. |
| 4,705,038 | A | 11/1987 | Sjostrom et al. |
| 4,722,685 | A | 2/1988 | de Estrada et al. |
| 4,823,807 | A | 4/1989 | Russell et al. |
| 4,874,181 | A | 10/1989 | Hsu |
| 5,129,118 | A | 7/1992 | Walmesley |
| 5,129,570 | A | 7/1992 | Schulze et al. |
| 5,152,744 | A | 10/1992 | Krause et al. |
| 5,301,061 | A | 4/1994 | Nakada et al. |
| 5,312,023 | A * | 5/1994 | Green ........ A61B 17/07207 227/175.1 |
| 5,326,013 | A | 7/1994 | Green et al. |
| 5,350,355 | A | 9/1994 | Sklar |
| 5,381,943 | A * | 1/1995 | Allen ........ A61B 17/0682 227/177.1 |
| 5,383,874 | A | 1/1995 | Jackson et al. |
| 5,383,880 | A | 1/1995 | Hooven |
| 5,389,098 | A | 2/1995 | Tsuruta et al. |
| 5,395,033 | A | 3/1995 | Byrne et al. |
| 5,400,267 | A | 3/1995 | Denen et al. |
| 5,411,508 | A | 5/1995 | Bessler et al. |
| 5,413,267 | A | 5/1995 | Solyntjes et al. |
| 5,427,087 | A | 6/1995 | Ito et al. |
| 5,431,323 | A * | 7/1995 | Smith ........ A61B 17/0682 227/177.1 |
| 5,467,911 | A | 11/1995 | Tsuruta et al. |
| 5,476,379 | A | 12/1995 | Disel |
| 5,487,499 | A | 1/1996 | Sorrentino et al. |
| 5,518,163 | A | 5/1996 | Hooven |
| 5,518,164 | A | 5/1996 | Hooven |
| 5,526,822 | A | 6/1996 | Burbank et al. |
| 5,529,235 | A | 6/1996 | Boiarski et al. |
| 5,535,934 | A | 7/1996 | Boiarski et al. |
| 5,535,937 | A | 7/1996 | Boiarski et al. |
| 5,540,375 | A | 7/1996 | Bolanos et al. |
| 5,540,706 | A | 7/1996 | Aust et al. |
| 5,542,594 | A | 8/1996 | McKean et al. |
| 5,562,239 | A | 10/1996 | Boiarski et al. |
| 5,632,432 | A | 5/1997 | Schulze et al. |
| 5,653,374 | A | 8/1997 | Young et al. |
| 5,658,300 | A | 8/1997 | Bito et al. |
| 5,667,517 | A | 9/1997 | Hooven |
| 5,693,042 | A | 12/1997 | Boiarski et al. |
| 5,704,534 | A | 1/1998 | Huitema et al. |
| 5,713,505 | A | 2/1998 | Huitema |
| 5,762,603 | A | 6/1998 | Thompson |
| 5,779,130 | A | 7/1998 | Alesi et al. |
| 5,782,396 | A | 7/1998 | Mastri et al. |
| 5,782,397 | A | 7/1998 | Koukline |
| 5,820,009 | A | 10/1998 | Melling et al. |
| 5,863,159 | A | 1/1999 | Lasko |
| 5,865,361 | A * | 2/1999 | Milliman ........ A61B 17/07207 227/176.1 |
| 5,908,427 | A | 6/1999 | McKean et al. |
| 5,954,259 | A | 9/1999 | Viola et al. |
| 5,964,774 | A | 10/1999 | McKean et al. |
| 5,993,454 | A | 11/1999 | Longo |
| 6,010,054 | A | 1/2000 | Johnson et al. |
| 6,017,354 | A | 1/2000 | Culp et al. |
| 6,032,849 | A | 3/2000 | Mastri et al. |
| 6,045,560 | A | 4/2000 | McKean et al. |
| 6,090,123 | A | 7/2000 | Culp et al. |
| 6,126,651 | A | 10/2000 | Mayer |
| 6,129,547 | A | 10/2000 | Cise et al. |
| 6,239,732 | B1 | 5/2001 | Cusey |
| 6,241,139 | B1 | 6/2001 | Milliman et al. |
| 6,264,086 | B1 | 7/2001 | McGuckin, Jr. |
| 6,264,087 | B1 | 7/2001 | Whitman |
| 6,302,311 | B1 | 10/2001 | Adams et al. |
| 6,315,184 | B1 | 11/2001 | Whitman |
| 6,321,855 | B1 | 11/2001 | Barnes |
| 6,329,778 | B1 | 12/2001 | Culp et al. |
| 6,343,731 | B1 | 2/2002 | Adams et al. |
| 6,348,061 | B1 | 2/2002 | Whitman |
| 6,368,324 | B1 | 4/2002 | Dinger et al. |
| 6,371,909 | B1 | 4/2002 | Hoeg et al. |
| 6,434,507 | B1 | 8/2002 | Clayton et al. |
| 6,443,973 | B1 | 9/2002 | Whitman |
| 6,461,372 | B1 | 10/2002 | Jensen et al. |
| 6,488,197 | B1 | 12/2002 | Whitman |
| 6,491,201 | B1 | 12/2002 | Whitman |
| 6,533,157 | B1 | 3/2003 | Whitman |
| 6,537,280 | B2 | 3/2003 | Dinger et al. |
| 6,610,066 | B2 | 8/2003 | Dinger et al. |
| 6,611,793 | B1 | 8/2003 | Burnside et al. |
| 6,645,218 | B1 | 11/2003 | Cassidy et al. |
| 6,654,999 | B2 | 12/2003 | Stoddard et al. |
| 6,698,643 | B2 | 3/2004 | Whitman |
| 6,699,177 | B1 | 3/2004 | Wang et al. |
| 6,716,233 | B1 | 4/2004 | Whitman |
| 6,783,533 | B2 | 8/2004 | Green et al. |
| 6,792,390 | B1 | 9/2004 | Burnside et al. |
| 6,793,652 | B1 | 9/2004 | Whitman et al. |
| 6,817,508 | B1 | 11/2004 | Racenet et al. |
| 6,830,174 | B2 | 12/2004 | Hillstead et al. |
| 6,846,308 | B2 | 1/2005 | Whitman et al. |
| 6,846,309 | B2 | 1/2005 | Whitman et al. |
| 6,849,071 | B2 | 2/2005 | Whitman et al. |
| 6,905,057 | B2 | 6/2005 | Swayze et al. |
| 6,959,852 | B2 | 11/2005 | Shelton, IV et al. |
| 6,964,363 | B2 | 11/2005 | Wales et al. |
| 6,981,628 | B2 | 1/2006 | Wales |
| 6,981,941 | B2 | 1/2006 | Whitman et al. |
| 6,986,451 | B1 | 1/2006 | Mastri et al. |
| 6,988,649 | B2 | 1/2006 | Shelton, IV et al. |
| 7,032,798 | B2 | 4/2006 | Whitman et al. |
| RE39,152 | E | 6/2006 | Aust et al. |
| 7,055,731 | B2 | 6/2006 | Shelton, IV et al. |
| 7,059,508 | B2 | 6/2006 | Shelton, IV et al. |
| 7,077,856 | B2 | 7/2006 | Whitman |
| 7,111,769 | B2 | 9/2006 | Wales et al. |
| 7,122,029 | B2 | 10/2006 | Koop et al. |
| 7,140,528 | B2 | 11/2006 | Shelton, IV |
| 7,143,923 | B2 | 12/2006 | Shelton, IV et al. |
| 7,143,925 | B2 | 12/2006 | Shelton, IV et al. |
| 7,143,926 | B2 | 12/2006 | Shelton, IV et al. |
| 7,147,138 | B2 | 12/2006 | Shelton, IV |
| 7,159,750 | B2 * | 1/2007 | Racenet ........ A61B 17/07207 227/180.1 |
| 7,172,104 | B2 | 2/2007 | Scirica et al. |
| 7,225,964 | B2 | 6/2007 | Mastri et al. |
| 7,238,021 | B1 | 7/2007 | Johnson |
| 7,246,734 | B2 | 7/2007 | Shelton, IV |
| 7,328,828 | B2 | 2/2008 | Ortiz et al. |
| 7,364,061 | B2 | 4/2008 | Swayze et al. |
| 7,380,695 | B2 | 6/2008 | Doll et al. |
| 7,380,696 | B2 | 6/2008 | Shelton, IV et al. |
| 7,404,508 | B2 | 7/2008 | Smith et al. |
| 7,407,078 | B2 | 8/2008 | Shelton, IV et al. |
| 7,416,101 | B2 | 8/2008 | Shelton, IV et al. |
| 7,419,080 | B2 | 9/2008 | Smith et al. |
| 7,422,139 | B2 | 9/2008 | Shelton, IV et al. |

(56) References Cited

U.S. PATENT DOCUMENTS

| | | |
|---|---|---|
| 7,431,189 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,464,846 B2 | 12/2008 | Shelton, IV et al. |
| 7,464,847 B2 | 12/2008 | Viola et al. |
| 7,464,849 B2 | 12/2008 | Shelton et al. |
| 7,481,347 B2 | 1/2009 | Roy |
| 7,481,824 B2 | 1/2009 | Boudreaux et al. |
| 7,487,899 B2 | 2/2009 | Shelton, IV et al. |
| 7,549,564 B2 | 6/2009 | Boudreaux |
| 7,565,993 B2 | 7/2009 | Milliman et al. |
| 7,568,603 B2 | 8/2009 | Shelton, IV et al. |
| 7,575,144 B2 * | 8/2009 | Ortiz ............... A61B 17/07207 227/175.1 |
| 7,588,176 B2 | 9/2009 | Timm et al. |
| 7,597,229 B2 * | 10/2009 | Boudreaux .......... A61B 17/072 227/175.1 |
| 7,637,409 B2 | 12/2009 | Marczyk |
| 7,641,093 B2 | 1/2010 | Doll et al. |
| 7,644,848 B2 | 1/2010 | Swayze et al. |
| 7,670,334 B2 | 3/2010 | Hueil et al. |
| 7,673,780 B2 | 3/2010 | Shelton, IV et al. |
| 7,699,835 B2 | 4/2010 | Lee et al. |
| 7,721,931 B2 | 5/2010 | Shelton, IV et al. |
| 7,740,159 B2 | 6/2010 | Shelton, IV et al. |
| 7,743,960 B2 | 6/2010 | Whitman et al. |
| 7,758,613 B2 | 7/2010 | Whitman |
| 7,766,210 B2 | 8/2010 | Shelton, IV et al. |
| 7,770,773 B2 | 8/2010 | Whitman et al. |
| 7,770,774 B2 * | 8/2010 | Mastri ............... A61B 17/07207 227/176.1 |
| 7,770,775 B2 | 8/2010 | Shelton et al. |
| 7,793,812 B2 | 9/2010 | Moore et al. |
| 7,799,039 B2 | 9/2010 | Shelton, IV et al. |
| 7,802,712 B2 | 9/2010 | Milliman et al. |
| 7,822,458 B2 | 10/2010 | Webster, III et al. |
| 7,845,534 B2 | 12/2010 | Viola et al. |
| 7,845,535 B2 * | 12/2010 | Scircia ............. A61B 17/07207 227/176.1 |
| 7,845,537 B2 | 12/2010 | Shelton, IV et al. |
| 7,857,185 B2 | 12/2010 | Swayze et al. |
| 7,870,989 B2 | 1/2011 | Viola et al. |
| 7,905,897 B2 | 3/2011 | Whitman et al. |
| 7,909,220 B2 * | 3/2011 | Viola ............... A61B 17/07207 227/175.1 |
| 7,918,230 B2 | 4/2011 | Whitman et al. |
| 7,922,719 B2 | 4/2011 | Ralph et al. |
| 7,947,034 B2 | 5/2011 | Whitman |
| 7,951,071 B2 | 5/2011 | Whitman et al. |
| 7,954,682 B2 | 6/2011 | Giordano et al. |
| 7,959,051 B2 * | 6/2011 | Smith ............... A61B 17/07207 227/175.1 |
| 7,963,433 B2 | 6/2011 | Whitman et al. |
| 7,967,178 B2 | 6/2011 | Scirica et al. |
| 7,967,179 B2 | 6/2011 | Olson et al. |
| 7,992,758 B2 | 8/2011 | Whitman et al. |
| 8,016,178 B2 | 9/2011 | Olson et al. |
| 8,016,855 B2 | 9/2011 | Whitman et al. |
| 8,020,743 B2 | 9/2011 | Shelton, IV |
| 8,025,199 B2 * | 9/2011 | Whitman ............. A61B 17/115 227/155 |
| 8,052,024 B2 | 11/2011 | Viola et al. |
| 8,056,787 B2 | 11/2011 | Boudreaux et al. |
| 8,114,118 B2 | 2/2012 | Knodel et al. |
| 8,132,705 B2 | 3/2012 | Viola et al. |
| 8,152,516 B2 | 4/2012 | Harvey et al. |
| 8,157,150 B2 | 4/2012 | Viola et al. |
| 8,157,151 B2 | 4/2012 | Ingmanson et al. |
| 8,182,494 B1 | 5/2012 | Yencho et al. |
| 8,186,555 B2 | 5/2012 | Shelton, IV et al. |
| 8,186,587 B2 | 5/2012 | Zmood et al. |
| 8,220,367 B2 | 7/2012 | Hsu |
| 8,235,273 B2 | 8/2012 | Olson et al. |
| 8,241,322 B2 | 8/2012 | Whitman et al. |
| 8,272,554 B2 | 9/2012 | Whitman et al. |
| 8,292,150 B2 | 10/2012 | Bryant |
| 8,292,888 B2 | 10/2012 | Whitman |
| 8,303,581 B2 | 11/2012 | Arts et al. |
| 8,336,754 B2 * | 12/2012 | Cappola ............. A61B 17/068 227/175.2 |
| 8,342,379 B2 | 1/2013 | Whitman et al. |
| 8,353,440 B2 | 1/2013 | Whitman et al. |
| 8,357,144 B2 | 1/2013 | Whitman et al. |
| 8,365,633 B2 | 2/2013 | Simaan et al. |
| 8,365,972 B2 | 2/2013 | Aranyi |
| 8,371,492 B2 | 2/2013 | Aranyi et al. |
| 8,372,057 B2 | 2/2013 | Cude et al. |
| 8,391,957 B2 | 3/2013 | Carlson et al. |
| 8,424,739 B2 | 4/2013 | Racenet et al. |
| 8,454,585 B2 | 6/2013 | Whitman |
| 8,505,802 B2 | 8/2013 | Viola et al. |
| 8,517,241 B2 | 8/2013 | Nicholas et al. |
| 8,540,733 B2 * | 9/2013 | Whitman ............ A61B 17/07207 227/178.1 |
| 8,551,076 B2 | 10/2013 | Duval et al. |
| 8,561,871 B2 | 10/2013 | Rajappa et al. |
| 8,616,431 B2 * | 12/2013 | Timm .............. A61B 19/2203 227/175.1 |
| 8,623,000 B2 | 1/2014 | Humayun et al. |
| 8,632,463 B2 | 1/2014 | Drinan et al. |
| 8,647,258 B2 | 2/2014 | Aranyi et al. |
| 8,657,174 B2 | 2/2014 | Yates et al. |
| 8,672,209 B2 * | 3/2014 | Crainich .......... A61B 17/07207 227/178.1 |
| 8,696,552 B2 | 4/2014 | Whitman |
| 8,708,213 B2 | 4/2014 | Shelton, IV et al. |
| 8,752,749 B2 | 6/2014 | Moore et al. |
| 8,783,541 B2 * | 7/2014 | Shelton, IV ...... A61B 17/07207 227/175.1 |
| 8,806,973 B2 | 8/2014 | Ross et al. |
| 8,851,355 B2 | 10/2014 | Aranyi et al. |
| 8,858,571 B2 | 10/2014 | Shelton, IV et al. |
| 8,967,443 B2 | 3/2015 | McCuen |
| 2003/0038938 A1 | 2/2003 | Jung et al. |
| 2003/0109898 A1 * | 6/2003 | Schwarz ............ A61B 17/2909 606/205 |
| 2004/111012 A1 | 6/2004 | Whitman |
| 2004/0133189 A1 | 7/2004 | Sakurai |
| 2004/0176751 A1 | 9/2004 | Weitzner et al. |
| 2005/0006431 A1 * | 1/2005 | Shelton ............. A61B 17/07207 227/175.1 |
| 2005/0103819 A1 * | 5/2005 | Racenet ........... A61B 17/07207 227/175.1 |
| 2005/0131442 A1 | 6/2005 | Yachia et al. |
| 2005/0143774 A1 * | 6/2005 | Polo ................... A61B 17/0469 606/205 |
| 2006/0079889 A1 * | 4/2006 | Scott .................. A61B 17/3201 606/45 |
| 2006/0142656 A1 | 6/2006 | Malackowski et al. |
| 2006/0278680 A1 | 12/2006 | Viola et al. |
| 2007/0023477 A1 * | 2/2007 | Whitman .......... A61B 17/07207 227/175.1 |
| 2007/0027469 A1 * | 2/2007 | Smith .............. A61B 17/07207 606/205 |
| 2007/0029363 A1 | 2/2007 | Popov |
| 2007/0055219 A1 | 3/2007 | Whitman et al. |
| 2007/0084897 A1 | 4/2007 | Shelton, IV et al. |
| 2007/0102472 A1 | 5/2007 | Shelton, IV |
| 2007/0152014 A1 | 7/2007 | Gillum et al. |
| 2007/0175949 A1 | 8/2007 | Shelton, IV et al. |
| 2007/0175950 A1 * | 8/2007 | Shelton, IV ...... A61B 17/07207 227/176.1 |
| 2007/0175951 A1 | 8/2007 | Shelton, IV et al. |
| 2007/0175955 A1 | 8/2007 | Shelton, IV et al. |
| 2007/0175961 A1 * | 8/2007 | Shelton, IV ...... A61B 17/07207 227/178.1 |
| 2007/0179476 A1 * | 8/2007 | Shelton, IV ...... A61B 17/07207 606/1 |
| 2008/0029570 A1 | 2/2008 | Shelton, IV et al. |
| 2008/0029573 A1 | 2/2008 | Shelton, IV et al. |
| 2008/0029574 A1 | 2/2008 | Shelton, IV et al. |
| 2008/0029575 A1 | 2/2008 | Shelton, IV et al. |
| 2008/0058801 A1 | 3/2008 | Taylor et al. |
| 2008/0109012 A1 | 5/2008 | Falco et al. |

(56) References Cited

U.S. PATENT DOCUMENTS

| | | |
|---|---|---|
| 2008/0110958 A1 | 5/2008 | McKenna et al. |
| 2008/0185419 A1 | 8/2008 | Smith et al. |
| 2008/0188841 A1 | 8/2008 | Tomasello et al. |
| 2008/0197167 A1 | 8/2008 | Viola et al. |
| 2008/0208195 A1 | 8/2008 | Shores et al. |
| 2008/0251561 A1 | 10/2008 | Eades et al. |
| 2008/0255413 A1 | 10/2008 | Zemlok et al. |
| 2008/0255607 A1 | 10/2008 | Zemlok |
| 2008/0257935 A1* | 10/2008 | Viola ............... A61B 17/07207 227/176.1 |
| 2008/0262654 A1 | 10/2008 | Omori et al. |
| 2008/0308603 A1 | 12/2008 | Shelton et al. |
| 2009/0090763 A1 | 4/2009 | Zemlok et al. |
| 2009/0095790 A1* | 4/2009 | Whitman ......... A61B 17/07207 227/175.1 |
| 2009/0099876 A1 | 4/2009 | Whitman |
| 2009/0101692 A1* | 4/2009 | Whitman ......... A61B 17/07207 227/175.1 |
| 2009/0112230 A1* | 4/2009 | Jinno ..................... A61B 19/22 606/130 |
| 2009/0171147 A1 | 7/2009 | Lee et al. |
| 2009/0179063 A1* | 7/2009 | Milliman ........... A61B 17/1114 227/175.1 |
| 2009/0182193 A1* | 7/2009 | Whitman ............ A61B 1/00101 600/104 |
| 2009/0209990 A1 | 8/2009 | Yates et al. |
| 2009/0216248 A1* | 8/2009 | Uenohara ............... A61B 17/29 606/130 |
| 2009/0254094 A1 | 10/2009 | Knapp et al. |
| 2009/0312773 A1* | 12/2009 | Cabrera ............. A61B 17/0469 606/144 |
| 2009/0314821 A1* | 12/2009 | Racenet ........... A61B 17/07207 227/180.1 |
| 2010/0010512 A1* | 1/2010 | Taylor .................... A61B 17/04 606/144 |
| 2010/0069942 A1 | 3/2010 | Shelton, IV |
| 2010/0072254 A1* | 3/2010 | Aranyi ............. A61B 17/07207 227/176.1 |
| 2010/0193568 A1* | 8/2010 | Scheib ............. A61B 17/07207 227/176.1 |
| 2010/0225073 A1 | 9/2010 | Porter et al. |
| 2011/0006101 A1 | 1/2011 | Hall et al. |
| 2011/0017801 A1 | 1/2011 | Zemlok et al. |
| 2011/0040308 A1* | 2/2011 | Cabrera ............. A61B 17/0469 606/144 |
| 2011/0077673 A1 | 3/2011 | Grubac et al. |
| 2011/0121049 A1 | 5/2011 | Malinouskas et al. |
| 2011/0125138 A1* | 5/2011 | Malinouskas ........ A61B 17/068 606/1 |
| 2011/0139851 A1 | 6/2011 | McCuen |
| 2011/0155783 A1 | 6/2011 | Rajappa et al. |
| 2011/0174099 A1* | 7/2011 | Ross .................... A61B 17/072 74/89.32 |
| 2011/0204119 A1 | 8/2011 | McCuen |
| 2011/0218522 A1 | 9/2011 | Whitman |
| 2011/0253765 A1 | 10/2011 | Nicholas et al. |
| 2011/0290854 A1 | 12/2011 | Timm et al. |
| 2011/0295242 A1* | 12/2011 | Spivey ................ A61B 19/2203 606/1 |
| 2011/0295269 A1 | 12/2011 | Swensgard et al. |
| 2012/0000962 A1 | 1/2012 | Racenet et al. |
| 2012/0074199 A1 | 3/2012 | Olson et al. |
| 2012/0089131 A1* | 4/2012 | Zemlok ........... A61B 17/07207 606/1 |
| 2012/0143002 A1 | 6/2012 | Aranyi et al. |
| 2012/0172924 A1 | 7/2012 | Allen, IV |
| 2012/0223121 A1* | 9/2012 | Viola .................... A61B 17/072 227/175.1 |
| 2012/0253329 A1 | 10/2012 | Zemlok et al. |
| 2012/0303002 A1 | 11/2012 | Chowaniec et al. |
| 2012/0310220 A1* | 12/2012 | Malkowski ............ A61B 17/29 606/1 |
| 2012/0323226 A1 | 12/2012 | Chowaniec et al. |
| 2013/0018361 A1 | 1/2013 | Bryant |
| 2013/0098966 A1* | 4/2013 | Kostrzewski ...... A61B 17/07207 227/176.1 |
| 2013/0098968 A1* | 4/2013 | Aranyi ............. A61B 17/07207 227/177.1 |
| 2013/0098969 A1* | 4/2013 | Scirica ............. A61B 17/07207 227/180.1 |
| 2013/0214025 A1 | 8/2013 | Zemlok et al. |
| 2013/0240596 A1 | 9/2013 | Whitman |
| 2013/0274722 A1 | 10/2013 | Kostrzewski et al. |
| 2013/0282052 A1 | 10/2013 | Aranyi et al. |
| 2013/0292451 A1 | 11/2013 | Viola et al. |
| 2013/0313304 A1 | 11/2013 | Shelton, IV et al. |
| 2013/0317486 A1 | 11/2013 | Nicholas et al. |
| 2013/0334278 A1* | 12/2013 | Kerr ................. A61B 17/07207 227/175.1 |
| 2014/0001231 A1* | 1/2014 | Shelton, IV ...... A61B 17/07207 227/175.3 |
| 2014/0005718 A1* | 1/2014 | Shelton, IV ...... A61B 17/07207 606/205 |
| 2014/0025046 A1* | 1/2014 | Williams .......... A61B 17/07207 606/1 |
| 2014/0100558 A1* | 4/2014 | Schmitz ............. A61B 17/3478 606/33 |
| 2014/0110455 A1 | 4/2014 | Ingmanson et al. |
| 2014/0207182 A1 | 7/2014 | Zergiebel et al. |
| 2014/0236173 A1 | 8/2014 | Scirica et al. |
| 2014/0236174 A1 | 8/2014 | Williams et al. |
| 2014/0246473 A1* | 9/2014 | Auld .................... A61B 17/068 227/175.1 |
| 2014/0246479 A1* | 9/2014 | Baber ................... A61B 17/068 227/180.1 |
| 2014/0276932 A1 | 9/2014 | Williams et al. |
| 2014/0299647 A1 | 10/2014 | Scirica et al. |
| 2014/0303668 A1 | 10/2014 | Nicholas et al. |
| 2014/0305994 A1* | 10/2014 | Parihar ................. A61B 17/068 227/180.1 |
| 2014/0358129 A1 | 12/2014 | Zergiebel et al. |
| 2014/0361068 A1 | 12/2014 | Aranyi et al. |
| 2014/0373652 A1 | 12/2014 | Zergiebel et al. |
| 2015/0048144 A1 | 2/2015 | Whitman |
| 2015/0076205 A1 | 3/2015 | Zergiebel |
| 2015/0080912 A1 | 3/2015 | Sapre |

FOREIGN PATENT DOCUMENTS

| | | | |
|---|---|---|---|
| CN | 101856251 A | 10/2010 | |
| CN | 102247182 A | 11/2011 | |
| DE | WO 0006033 A1 * | 2/2000 | ......... A61B 17/2909 |
| DE | 102008053842 A1 | 5/2010 | |
| EP | 0634144 | 1/1995 | |
| EP | 0648476 A1 | 4/1995 | |
| EP | 0686374 A2 | 12/1995 | |
| EP | 0705571 A1 | 4/1996 | |
| EP | 1690502 | 8/2006 | |
| EP | 1723913 A1 | 11/2006 | |
| EP | 1736112 | 12/2006 | |
| EP | 1759652 A2 | 3/2007 | |
| EP | 1769754 | 4/2007 | |
| EP | 1772105 A1 | 4/2007 | |
| EP | 1 813 211 | 8/2007 | |
| EP | 1813199 A1 | 8/2007 | |
| EP | 1813203 | 8/2007 | |
| EP | 1813211 A2 * | 8/2007 | ....... A61B 17/07207 |
| EP | 1908412 A2 | 4/2008 | |
| EP | 1917929 A1 | 5/2008 | |
| EP | 1943954 A2 | 7/2008 | |
| EP | 1943956 A2 | 7/2008 | |
| EP | 1943958 | 7/2008 | |
| EP | 1943976 | 7/2008 | |
| EP | 1952769 A2 | 8/2008 | |
| EP | 2005898 A2 | 12/2008 | |
| EP | 2027819 | 2/2009 | |
| EP | 2044890 A1 | 4/2009 | |
| EP | 2055243 | 5/2009 | |
| EP | 2090247 A1 | 8/2009 | |
| EP | 2098170 | 9/2009 | |
| EP | 2100561 | 9/2009 | |
| EP | 2100562 A2 | 9/2009 | |
| EP | 2165664 A2 | 3/2010 | |

(56) References Cited

FOREIGN PATENT DOCUMENTS

| | | | |
|---|---|---|---|
| EP | 2236098 A2 | 10/2010 | |
| EP | 2245994 A1 | 11/2010 | |
| EP | 2263568 A2 | 12/2010 | |
| EP | 2272443 A1 | 1/2011 | |
| EP | 2316345 A1 | 5/2011 | |
| EP | 2324776 A2 | 5/2011 | |
| EP | 2329773 A1 | 6/2011 | |
| EP | 2333509 A1 | 6/2011 | |
| EP | 2377472 A1 | 10/2011 | |
| EP | 2462878 A1 | 6/2012 | |
| EP | 2462880 A2 | 6/2012 | |
| EP | 2491872 A1 | 8/2012 | |
| EP | 2586382 A2 | 5/2013 | |
| EP | 2606834 A2 | 6/2013 | |
| EP | 2676615 A2 | 12/2013 | |
| EP | 2815705 A1 | 12/2014 | |
| ES | 2333509 A1 | 2/2010 | |
| FR | 2861574 A1 | 5/2005 | |
| JP | 08-038488 | 2/1996 | |
| JP | 2005-125075 A | 5/2005 | |
| KR | 20120022521 A | 3/2012 | |
| WO | 99/15086 A1 | 4/1999 | |
| WO | WO 00/72760 | 12/2000 | |
| WO | WO 00/72765 | 12/2000 | |
| WO | 03/000138 A2 | 1/2003 | |
| WO | 03/030743 A2 | 4/2003 | |
| WO | WO 03/026511 | 4/2003 | |
| WO | 03065916 A1 | 8/2003 | |
| WO | WO 03/077769 | 9/2003 | |
| WO | 03090630 A2 | 11/2003 | |
| WO | WO 2004/107989 | 12/2004 | |
| WO | WO 2006/042210 | 4/2006 | |
| WO | 2007016290 A2 | 2/2007 | |
| WO | WO 2007/014355 | 2/2007 | |
| WO | WO 2007/026354 | 3/2007 | |
| WO | 2007137304 A2 | 11/2007 | |
| WO | WO 2008/131362 | 10/2008 | |
| WO | WO 2008/133956 | 11/2008 | |
| WO | WO 2009/039506 | 3/2009 | |
| WO | WO 2009/132359 | 10/2009 | |
| WO | 2009/143092 A1 | 11/2009 | |
| WO | 2009149234 A1 | 12/2009 | |
| WO | 2011/108840 A2 | 9/2011 | |
| WO | 2012040984 A1 | 4/2012 | |
| WO | WO 2015088655 A1 * | 6/2015 | ............. A61B 17/29 |

OTHER PUBLICATIONS

Extended European Search Report from EP Application No. 13189026.1 dated Jan. 31, 2014.
The Extended European Search Report from Application No. EP 13177163.6 dated Feb. 6, 2014.
Extended European Search Report from Application No. EP 13175477.2 dated Feb. 6, 2014.
Extended European Search Report from Application No. EP 13169998.5 dated Feb. 24, 2014.
Extended European Search Report corresponding to EP 13176805.3, dated Nov. 4, 2013.
Extended European Search Report from Application No. EP 13171742.3 dated Jan. 3, 2014.
International Search Report corresponding to PCT/US2005/027266, completed May 30, 2008 and mailed Jun. 18, 2008; (2 pp.).
Extended European Search Report corresponding to EP 08 25 3184.9, completed Feb. 12, 2009 and mailed Feb. 27, 2009; (3 pp.).
Extended European Search Report corresponding to EP 10 25 0228.3, completed May 20, 2010 and mailed Jun. 1, 2010; (6 pp.).
Extended European Search Report corresponding to EP 10 25 2037.6, completed Mar. 1, 2011 and mailed Mar. 9, 2011; (3 pp.).
Extended European Search Report corresponding to EP 10 25 1968.3, completed on Jul. 4, 2011 and mailed Jul. 14, 2011; (12 pp.).
Extended European Search Report corresponding to EP 11 15 2266.0, completed Jul. 15, 2011 and mailed Jul. 28, 2011; (3 pp.).
Extended European Search Report corresponding to EP 11 25 0462.6, completed Jul. 20, 2011 and mailed Jul. 28, 2011; (6 pp.).
Extended European Search Report corresponding to EP 11 25 0771.0, completed Feb. 7, 2012 and mailed Feb. 17, 2012; (3 pp.).
Extended European Search Report corresponding to EP 06 78 8914.7, completed May 3, 2012 and mailed May 11, 2012; (8 pp.).
Partial European Search Report corresponding to EP 12 18 6177.7, completed Jan. 30, 2013 and mailed Feb. 12, 2013; (6 pp.).
Partial European Search Report corresponding to EP 13 17 2400.7, completed Sep. 18, 2013 and mailed Oct. 1, 2013; (7 pp).
Extended European Search Report corresponding to EP No. 11 17 8021.9, mailed Jun. 4, 2013; (3 pp).
Extended European Search Report corresponding to EP No. 13 16 3033.7, completed Jun. 27, 2013 and mailed Jul. 15, 2013; (8 pp).
Extended European Search Report corresponding to EP No. 12 18 6177.7, completed Aug. 14, 2013 and mailed Aug. 23, 2013; (8 pp).
Partial European Search Report corresponding to EP No. 13 17 1742.3, completed Sep. 17, 2013 and mailed Sep. 25, 2013; (8 pp).
Partial European Search Report corresponding to EP No. 13 17 2400.7, completed Sep. 18, 2013 and mailed Oct. 1, 2013; (7 pp).
Extended European Search Report corresponding to EP No. 13 17 5475.6, completed Sep. 23, 2013 and mailed Oct. 1, 2013; (8 pp).
Extended European Search Report corresponding to EP No. 13 17 5478.0, completed Sep. 24, 2013 and mailed Oct. 2, 2013; (6 pp).
Extended European Search Report corresponding to EP No. 13 17 5479.8, completed Sep. 27, 2013 and mailed Oct. 10, 2013; (7 pp).
Partial Extended European Search Report corresponding to EP 13 17 5477.2, completed Oct. 7, 2013 and mailed Oct. 15, 2013; (7 pp).
Extended European Search Report corresponding to EP No. 08 25 2703.7, completed Oct. 23, 2008 and mailed Oct. 31, 2008; (7 pp).
Extended European Search Report from EP Applicat No. 13172400.7 dated Jan. 21, 2014.
Extended European Search Report for EP 15 19 0245 dated Jan. 28, 2016.

* cited by examiner

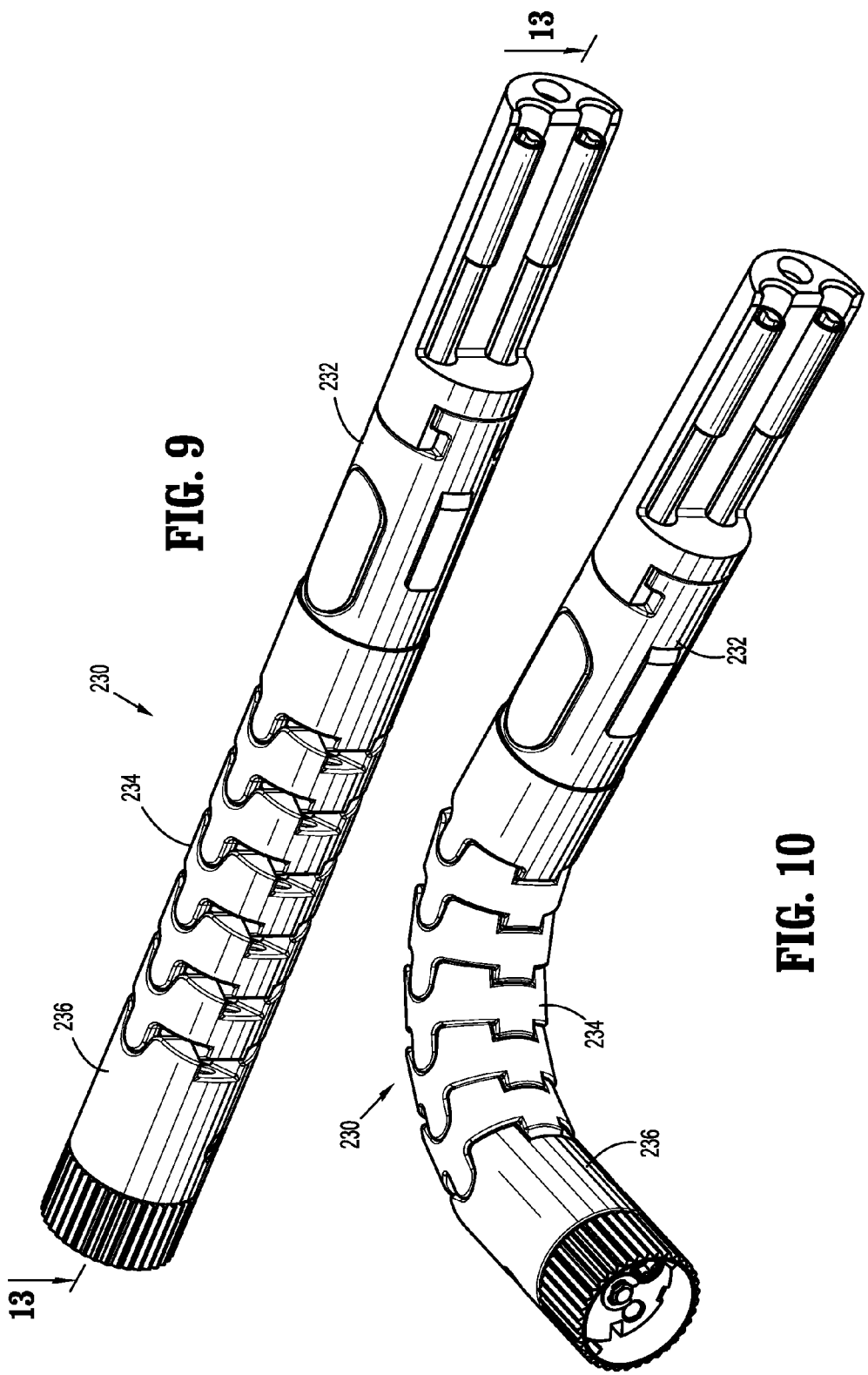

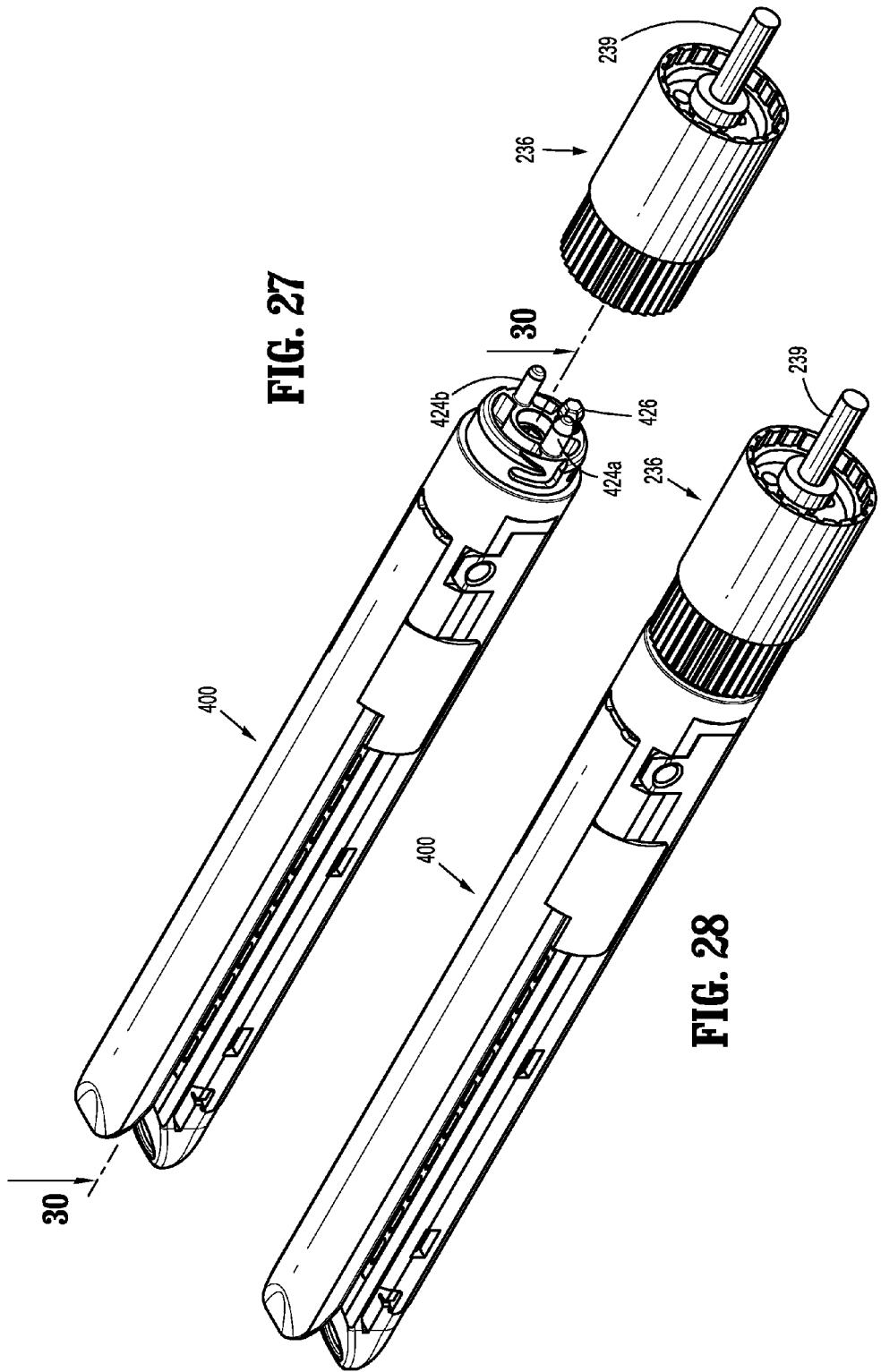

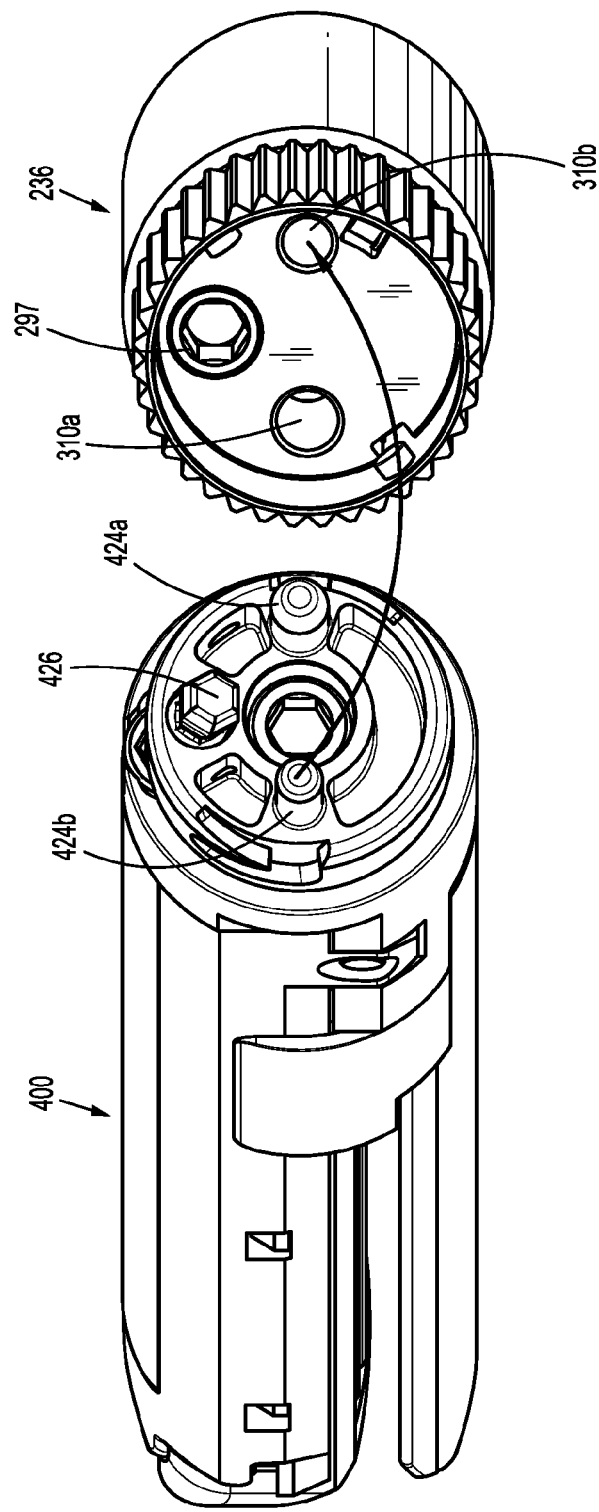

APPARATUS FOR ENDOSCOPIC PROCEDURES

CROSS-REFERENCE TO RELATED APPLICATIONS

This application claims the benefit of and priority to U.S. Provisional Patent Application No. 61/661,461, filed Jun. 19, 2012, the entire disclosure of which is incorporated by reference herein.

BACKGROUND

1. Technical Field

The present disclosure relates to surgical apparatus, devices and/or systems for performing endoscopic surgical procedures and methods of use thereof. More specifically, the present disclosure relates to electromechanical, hand-held surgical apparatus, devices and/or systems configured for use with removable disposable loading units and/or single use loading units for clamping, cutting and/or stapling tissue.

2. Background of Related Art

A proprietary drive system for operating and/or manipulating electromechanical surgical devices is known. Such electromechanical surgical devices can include a handle assembly, which is reusable, and replaceable loading units and/or single use loading units or the like that are selectively connected to the handle assembly prior to use and then disconnected from the handle assembly following use, in order to be disposed of or in some instances sterilized for re-use.

Electromechanical surgical devices can be relatively expensive to manufacture, purchase and/or operate. There is a desire by manufacturers and end users to develop electromechanical surgical devices that are relatively inexpensive to manufacture, purchase and/or operate.

Accordingly, a need exists for electromechanical surgical apparatus, devices and/or systems that are relatively economical to develop and manufacture, to store and ship, as well as economical and convenient to purchase and use from the end user's perspective.

An additional need exists for the electromechanical surgical apparatus to incorporate a connection assembly that reduces the number of drive cables required to drive multiple features of the apparatus. There is also an interest in reducing the number of drive cables that extend through an articulating neck assembly.

SUMMARY

The present disclosure relates to electromechanical, hand-held surgical apparatus, devices and/or systems configured for use with removable disposable loading units and/or single use loading units for clamping, cutting and/or stapling tissue.

According to an aspect of the present disclosure, an electromechanical surgical system is provided and includes a surgical instrument including an instrument housing defining a connecting portion for selectively connecting with a shaft assembly, the surgical instrument having at least one rotatable drive member; an end effector configured to perform at least one function; and wherein the shaft assembly is arranged for selectively interconnecting the end effector and the surgical device. The shaft assembly includes a transmission housing configured and adapted for selective connection to the connecting portion of the surgical device and to be in operative communication with each of the at least one rotatable drive member of the surgical device; an outer tubular body having a proximal end supported by the transmission housing and a distal end configured and adapted for operative connection with the end effector; a distal neck housing for interconnecting a rotatable drive member of the surgical instrument and a rotation receiving member supported in the end effector, wherein the distal neck housing includes a first end that is connectable to one rotatable drive member of the surgical instrument and a second end that is connectable to the rotation receiving member of the end effector, wherein the force transmitting assembly transmits a rotation of the rotatable drive member of the surgical instrument to the rotation receiving member of the end effector. The distal neck assembly includes at least one gear system configured to convert a rotational input of the rotatable drive member into at least two output forces to the end effector; and an articulating neck assembly interconnecting the tubular body and the distal neck housing, wherein the articulating neck assembly is configured to enable off-axis articulation of the distal neck assembly, and wherein the rotatable drive member extends through the articulating neck assembly.

A first output force of the at least one gear system of the distal neck housing may result in a firing of the end effector. A first output force of the at least one gear system of the distal neck housing may result in a rotation of the end effector relative to the shaft assembly.

The distal neck housing may non-rotatably and slidably support a lock collar. The lock collar may be movable between a first position wherein the first output force of the at least one gear system of the distal neck housing results in the firing of the end effector, and wherein the first output force of the at least one gear system of the distal neck housing results in the rotation of the end effector relative to the shaft assembly.

The distal neck housing may include an outer tubular housing defining at least one tooth extending radially inward therefrom; and a first planetary gear system supported in the outer tubular housing. The first planetary gear system may include a first sun gear drivable by the one rotatable drive member of the surgical instrument; a ring gear rotatably supported in the outer tubular housing; at least one first planet gear interposed and inter-engaging the first sun gear and the ring gear; and a carrier rotatably supported in the outer tubular housing, the carrier including a respective stem rotatably supporting each first planet gear. In use, when the first sun gear rotates each first planet gear about an axis of rotation of first sun gear, the end effector may be fired. Also in use, when the first sun gear rotates each first planet gear about a respective axis of rotation, the end effector may be rotated.

The distal neck housing may include a crown gear non-rotatably connected to the carrier; and a lock collar gear axially, non-rotatably and slidably supported in the outer tubular housing. The lock collar gear may include a first position wherein the lock collar gear engages the crown gear and prevents the crown gear from rotating, wherein non-rotation of the crown gear permits the rotation of the end effector. The lock collar gear may include a second position wherein the lock collar gear is disengaged from the crown gear and permits the crown gear to rotating, wherein rotation of the crown gear permits the firing of the end effector.

The distal neck housing may include a rotation hub non-rotatably supported in outer tubular housing; and a second planetary gear system supported in the rotation hub. The second planetary gear system may include a second sun gear non-rotatably connected to the carrier; and at least one second planet gear rotatably supported in the rotation hub and inter-engaged with the second sun gear; and a firing connector connected to one of the at least one second planet gear, wherein the firing connector is configured to engage a force receiving member of the end effector. In use, when the carrier rotates, the second sun gear may be rotated to rotate the at least one second planet gear and to fire the end effector.

The surgical instrument may further include at least one drive motor supported in the instrument housing and being configured to rotate the at least one rotatable drive member; a battery disposed within the instrument housing for powering the at least one drive motor; and a circuit board disposed within the instrument housing for controlling power delivered from the battery to the motor.

The end effector may include an upper jaw and a lower jaw, at least one of the upper jaw and the lower jaw being movable in relation to the other of the upper jaw and the lower jaw.

The electromechanical surgical system may further include at least one surgical buttress releasably secured to a tissue contacting surface of at least one of the upper jaw and the lower jaw.

The electromechanical surgical system may further include a drive beam translatable through at least one of the upper jaw and the lower jaw to move the lower jaw relative to the upper jaw.

The end effector may include an upper jaw and a lower jaw, at least one of the upper jaw and the lower jaw being movable in relation to the other of the upper jaw and the lower jaw; a cartridge assembly supported in the lower jaw, the cartridge assembly including a plurality of staples therein; at least one surgical buttress releasably secured to a tissue contacting surface of at least one of the upper jaw and the lower jaw, the at least one surgical buttress secured to the at least one of the upper jaw and the lower jaw by at least one suture, the at least one of the upper jaw and the lower jaw being configured to receive a portion of the at least one suture.

The lower jaw of the end effector may be configured to selectively receive a cartridge assembly. The cartridge assembly may include a cartridge body defining a longitudinally extending knife slot; a plurality of staples disposed in individual staple retaining slots formed in the cartridge body, wherein the staple retaining slots are arranged in multiple longitudinally extending rows disposed on opposed lateral sides of the knife slot; an actuation sled slidably supported in the cartridge body and being configured to expel at least a portion of the plurality of staples from the cartridge body upon a distal movement of the actuation sled from a proximal-most position; and a knife sled slidably supported in the cartridge body at a location proximal of the actuation sled, wherein the knife sled includes a knife blade extending into the knife slot.

The drive beam may engage the knife sled and the actuation sled when the cartridge assembly is disposed in the lower jaw and when the drive beam is advanced.

The actuation sled of the cartridge assembly may remain in a distally advanced position following any retraction of the drive beam.

The knife sled of the cartridge assembly may include a lock-out spring extending therefrom, wherein the lock-out spring of the knife sled engages a lock-out notch defined in the cartridge body to inhibit advancement of the knife sled.

In use, when the actuation sled and the knife sled are in a proximal-most position, the actuation sled may block engagement of the lock-out spring of the knife sled with the lock-out notch of the cartridge body.

The knife sled of the cartridge assembly may be retracted upon any retraction of the drive beam.

The drive beam may include a lock clip extending therefrom. In use, the lock clip of the drive beam may engage the knife sled upon any distal advancement of the drive beam such that the knife sled retracts upon a retraction of the drive beam.

The at least one rotation receiving member of the end effector may include a drive screw rotatably supported in the lower jaw, wherein the drive beam is threadably supported on the drive screw, whereby rotation of the drive screw results in axial translation of the drive beam.

The at least one rotation receiving member of the end effector may include a drive screw rotatably supported in the lower jaw, wherein the drive beam is threadably supported on the drive screw, whereby rotation of the drive screw results in axial translation of the drive beam.

The at least one force transmitting assembly of the shaft assembly includes a first gear train system interconnecting the at least one rotatable drive member of the surgical instrument and the at least one rotation receiving member of the end effector. The first gear train system may vary at least one of a rate of rotation between the at least one rotatable drive member of the surgical instrument and the at least one rotation receiving member of the end effector; and an axis of rotation between the at least one rotatable drive member of the surgical instrument and the at least one rotation receiving member of the end effector.

The shaft assembly may include an articulating neck assembly, and wherein the first gear train system is disposed proximal of the articulating neck assembly.

The shaft assembly may include a neck housing disposed distal of the articulating neck assembly. The distal neck housing may support a neck first gear train of the at least one force transmitting assembly. The neck first gear train may interconnect an output of the first gear train system with the at least one rotation receiving member of the end effector. The neck first gear train may vary at least one of a rate of rotation between the output of the first gear train system and the at least one rotation receiving member of the end effector; and an axis of rotation between the output of the first gear train system and the at least one rotation receiving member of the end effector.

The at least one rotation receiving member of the end effector may include a drive screw rotatably supported in the lower jaw. The drive beam may be threadably supported on the drive screw, whereby rotation of the drive screw results in axial translation of the drive beam.

The at least one rotation receiving member of the end effector may include a drive screw rotatably supported in the lower jaw, wherein the drive beam is threadably supported on the drive screw, whereby rotation of the drive screw results in axial translation of the drive beam.

The at least one force transmitting assembly of the shaft assembly may include a second gear train system interconnecting another of the at least one rotatable drive member of the surgical instrument and a rotation hub rotatably supported at a distal end of the neck housing. The second gear train system may vary at least one of a rate of rotation between the another at least one rotatable drive member of the surgical instrument and the rotation hub of the shaft assembly; and an axis of rotation between the another at least one rotatable drive member of the surgical instrument and the rotation hub of the shaft assembly.

The shaft assembly may further include an articulating neck assembly supported at a distal end of the outer tube; a distal neck housing supported at a distal end of the articulating neck assembly, and first and second diametrically opposed articulation cables extending at least partially along the neck assembly. Each articulation cable may include a distal end anchored to the distal neck housing, and a proximal end extending into the outer tube, the proximal end of each articulation cable being secured to a respective first and second rack, each rack being operatively connected to one another by a spur gear. In use, axial displacement of the first rack in a first direction may result in axial displacement of the respective first articulation cable in the first direction; articulation of the neck assembly in a first off-axis direction; and axial displacement of the second articulation cable in a direction opposite to the first direction.

The shaft assembly may further include a threaded rod extending proximally from the first rack; and a threaded shaft threadably connected to the threaded rod extending from the first rack, the threaded shaft being connected to another at least one drive member of the surgical instrument. In use, rotation of the another at least one drive member of the surgical instrument imparts rotation to the threaded shaft and, in turn, axial displacement of the threaded rod and first rack.

The shaft assembly may further include an articulating neck assembly supported at a distal end of the outer tube, the neck assembly defining a central axis and being articulatable in a first plane; a distal neck housing supported at a distal end of the articulating neck assembly, first and second diametrically opposed articulation cables extending at least partially along the neck assembly; a first drive cable extending at least partially along the neck assembly and defining a first drive axis spaced a radial distance from the central axis, the first drive axis being defined by a first drive plane extending orthogonal to the first plane; and a second drive cable extending at least partially along the neck assembly and defining a second drive axis spaced a radial distance from the central axis, the second drive axis being defined by a second drive plane extending orthogonal to the first plane. In use, the first drive cable and the second drive cable are diametrically opposed to one another.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 9 is a perspective view of a neck assembly of the shaft assembly, shown in a straight orientation;

FIG. 10 is a perspective view of the neck assembly of FIG. 9, shown in an articulated condition;

FIGS. 27-29 are perspective views illustrating a connection of an end effector to the distal neck housing of FIGS. 14-26.

DETAILED DESCRIPTION OF EMBODIMENTS

Figure 1:
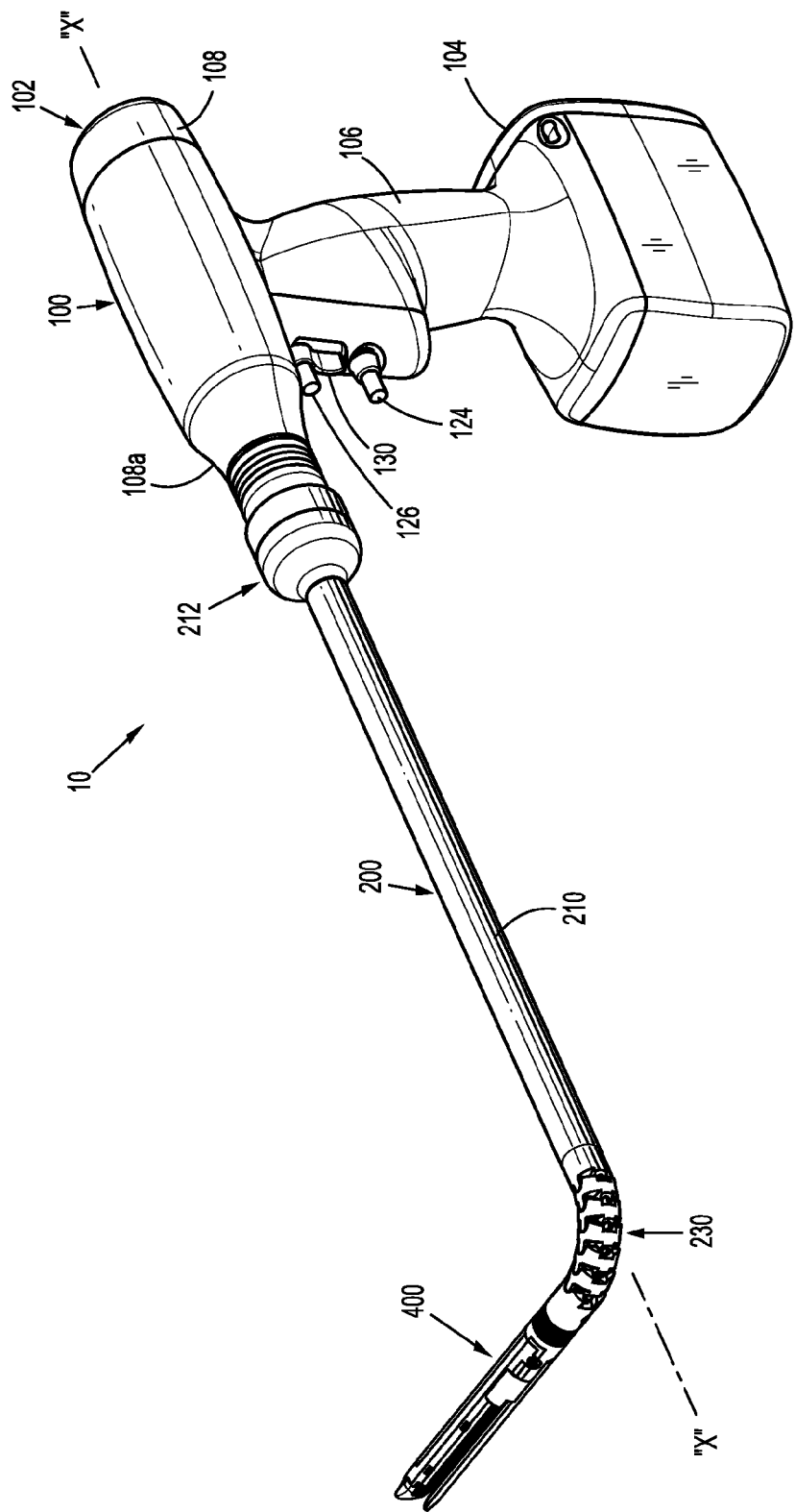
FIG. 1 is a perspective view of an electromechanical surgical system according to an embodiment of the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user.

Figure 2:
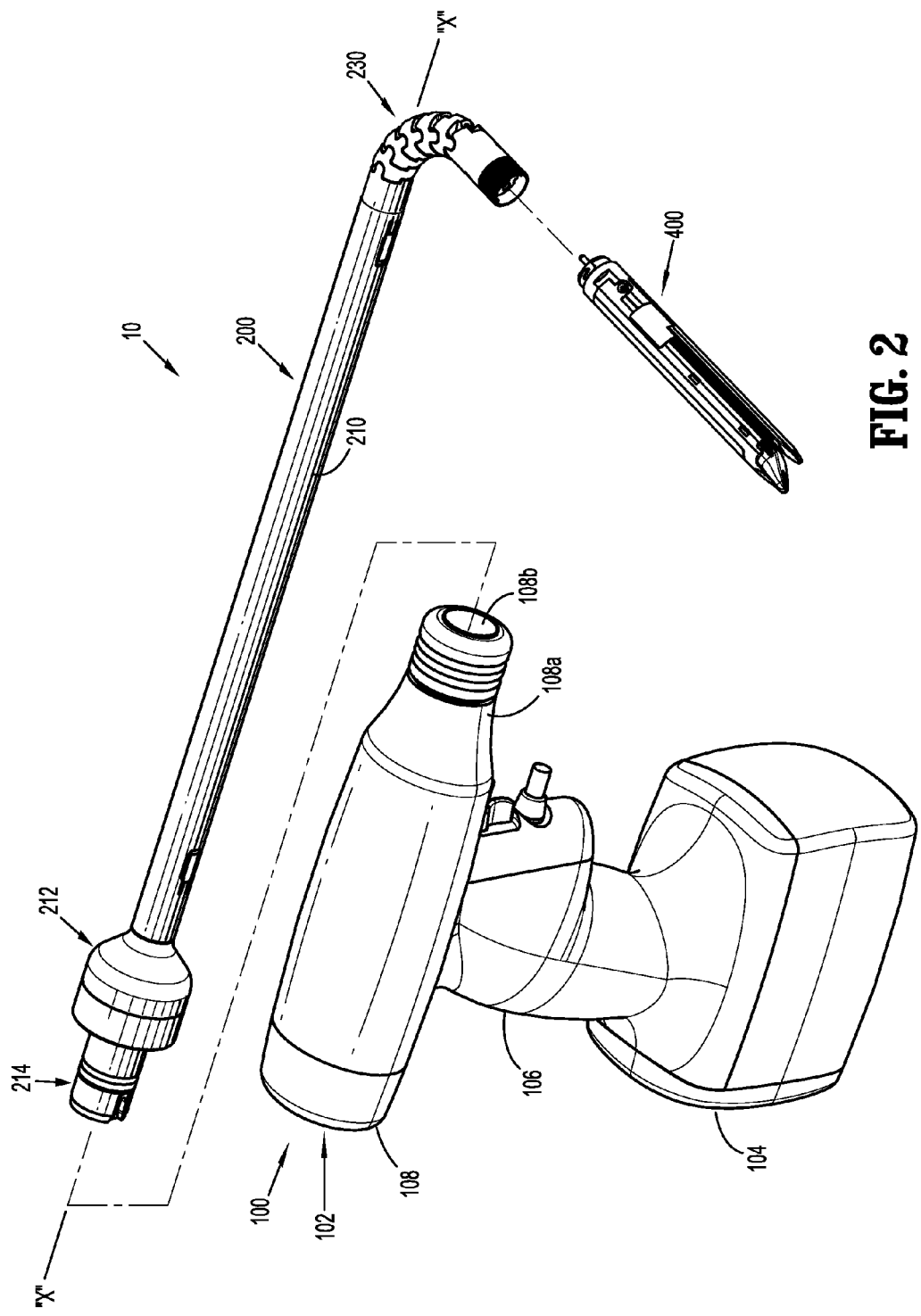
FIG. 2 is a perspective view, with parts separated, of the electromechanical surgical system of FIG. 1.
Figure 3:
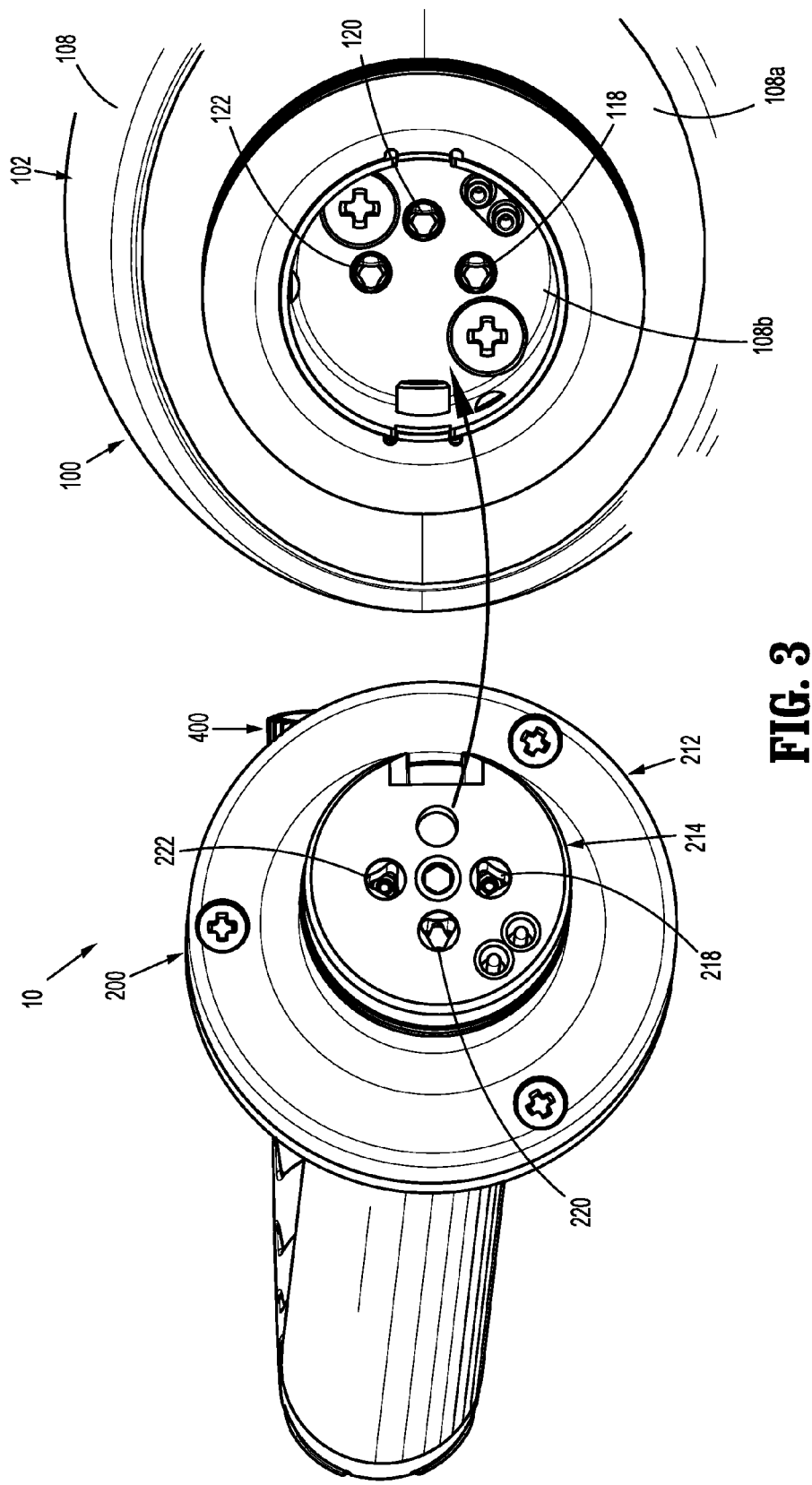
FIG. 3 is a rear, perspective view of a shaft assembly and a powered surgical instrument, of the electromechanical surgical system of FIGS. 1 and 2, illustrating a connection therebetween.

Referring initially to FIGS. 1-3, an electromechanical, powered surgical system, in accordance with an embodiment of the present disclosure is shown and generally designated 10. Electromechanical surgical system 10 includes a surgical apparatus or device in the form of an electromechanical, powered surgical instrument 100, which may be hand-held, and that is configured for selective attachment thereto of a plurality of different end effectors 400, via a shaft assembly 200, that are each configured for actuation and manipulation by the electromechanical, hand-held, powered surgical instrument 100. In particular, surgical instrument 100 is configured for selective connection with shaft assembly 200, and, in turn, shaft assembly 200 is configured for selective connection with any one of a plurality of different end effectors 400.

Reference may be made to International Application No. PCT/US2008/077249, filed Sep. 22, 2008 (Inter. Pub. No. WO 2009/039506) and U.S. patent application Ser. No. 12/622,827, filed on Nov. 20, 2009, the entire content of each of which are hereby incorporated herein by reference, for a detailed description of the construction and operation of exemplary electromechanical, hand-held, powered surgical instrument 100.

Generally, as illustrated in FIGS. 1-3, surgical instrument 100 includes an instrument housing 102 having a lower housing portion 104, an intermediate housing portion 106 extending from and/or supported on lower housing portion 104, and an upper housing portion 108 extending from and/or supported on intermediate housing portion 106. The surgical instrument 100 has a controller for controlling certain functions of the surgical system, collecting data, and performing other functions. Instrument housing 102 defines a cavity therein in which a circuit board (not shown) and a drive mechanism (not shown) are situated.

It is contemplated that the interior of the instrument housing can be entirely or partially encapsulated with a material to protect one or more components thereof. U.S. patent application Ser. No. 13/117,410, filed May 27, 2011, is hereby incorporated by reference in its entirety. The interior components of the instrument housing can be as disclosed in U.S. patent application Ser. No. 13/444,228, filed Apr. 11, 2012, and U.S. patent application Ser. No. 13/117,410, filed May 27, 2011, are hereby incorporated by reference in their entirety.

The circuit board is configured to control the various operations of surgical instrument 100, as will be set forth in additional detail below. In accordance with the present disclosure, instrument housing 102 provides a housing in which a rechargeable battery (not shown), is removably situated. The battery is configured to supply power to any of the electrical components of surgical instrument 100.

Upper housing portion 108 of instrument housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X" (see FIGS. 1 and 2), relative to instrument housing 102; to move an upper jaw or anvil assembly 442 of end effector 400 relative to a lower jaw 432 or cartridge assembly 410 of end effector 400; to articulate and/or rotate the shaft assembly; and/or to fire a stapling and cutting cartridge within cartridge assembly 410 of end effector 400.

Upper housing portion 108 of instrument housing 102 provides a housing in which the drive mechanism (not shown) is situated. The drive mechanism is configured to drive shafts and/or gear components in order to perform the various operations of surgical instrument 100. In particular, the drive mechanism is configured to drive shafts and/or gear components in order to selectively move end effector 400 relative to shaft assembly 200; to rotate anvil assembly 200 and/or end effector 400, about a longitudinal axis "X" (see FIGS. 1 and 2), relative to instrument housing 102; to move an upper jaw or anvil assembly 442 of end effector 400 relative to a lower jaw or cartridge assembly 432 of end effector 400; to articulate and/or rotate the shaft assembly; and/or to fire a stapling and cutting cartridge within cartridge assembly 432 of end effector 400.

The shaft assembly 200 has a force transmitting assembly for interconnecting the at least one drive member of the surgical instrument to at least one rotation receiving member of the end effector. The force transmitting assembly has a first end that is connectable to the at least one rotatable drive member and a second end that is connectable to the at least one rotation receiving member of the end effector. When shaft assembly 200 is mated to surgical instrument 100, each of rotatable drive members or connectors 118, 120, 122 of surgical instrument 100 couples with a corresponding rotatable connector sleeve 218, 220, 222 of shaft assembly 200 (see FIGS. 3 and 5). In this regard, the interface between corresponding first drive member or connector 118 and first connector sleeve 218, the interface between corresponding second drive member or connector 120 and second connector sleeve 220, and the interface between corresponding third drive member or connector 122 and third connector sleeve 222 are keyed such that rotation of each of drive members or connectors 118, 120, 122 of surgical instrument 100 causes a corresponding rotation of the corresponding connector sleeve 218, 220, 222 of shaft assembly 200.

The mating of drive members or connectors 118, 120, 122 of surgical instrument 100 with connector sleeves 218, 220, 222 of shaft assembly 200 allows rotational forces to be independently transmitted via each of the three respective connector interfaces. The drive members or connectors 118, 120, 122 of surgical instrument 100 are configured to be independently rotated by the drive mechanism. In this regard, the controller has a function selection module (not shown) of the drive mechanism selects which drive member or connector 118, 120, 122 of surgical instrument 100 is to be driven by an input drive component (not shown) of the drive mechanism.

Since each of drive members or connectors 118, 120, 122 of surgical instrument 100 has a keyed and/or substantially non-rotatable interface with respective connector sleeves 218, 220, 222 of shaft assembly 200, when shaft assembly 200 is coupled to surgical instrument 100, rotational force(s) are selectively transferred from the drive mechanism of surgical instrument 100 to shaft assembly 200, and on to end effector 400, as will be discussed in greater detail below.

The selective rotation of drive member(s) or connector(s) 118, 120 and/or 122 of surgical instrument 100 allows surgical instrument 100 to selectively actuate different functions of end effector 400. As will be discussed in greater detail below, selective and independent rotation of first drive member or connector 118 of surgical instrument 100 corresponds to the selective and independent opening and closing of end effector 400, and driving of a stapling/cutting component of end effector 400. Also, the selective and independent rotation of second drive member or connector 120 of surgical instrument 100 corresponds to the selective and independent articulation of end effector 400 transverse to longitudinal axis "X" (see FIG. 1). Additionally, the selective and independent rotation of third drive member or connector 122 of surgical instrument 100 corresponds to the selective and independent rotation of end effector 400 about longitudinal axis "X" (see FIG. 1) relative to instrument housing 102 of surgical instrument 100.

In accordance with the present disclosure, the drive mechanism may include a selector gearbox assembly (not shown); a function selection module (not shown), located proximal to the selector gearbox assembly, that functions to selectively move gear elements within the selector gearbox assembly into engagement with a second motor (not shown). The drive mechanism may be configured to selectively drive one of drive members or connectors 118, 120, 122 of surgical instrument 100, at a given time.

As illustrated in FIGS. 1 and 2, instrument housing 102 supports a pair of finger-actuated control buttons 124, 126 and/or rocker device(s) 130 (only one rocker device being shown). Each one of the control buttons 124, 126 and rocker device(s) 130 includes a respective magnet (not shown) that is moved by the actuation of an operator. In addition, the circuit board (not shown) housed in instrument housing 102 includes, for each one of the control buttons 124, 126 and rocker device(s) 130, respective Hall-effect switches (not shown) that are actuated by the movement of the magnets in the control buttons 124, 126 and rocker device(s) 130. In particular, located immediately proximal to the control button 124 is a respective Hall-effect switch (not shown) that is actuated upon the movement of a magnet within the control button 124 upon the operator actuating control button 124. The actuation of Hall-effect switch (not shown), corresponding to control button 124, causes the circuit board to provide appropriate signals to the function selection module and the input drive component of the drive mechanism to close end effector 400 and/or to fire a stapling/cutting cartridge within end effector 400.

Also, located immediately proximal to control button 126 is a respective Hall-effect switch (not shown) that is actuated upon the movement of a magnet (not shown) within control button 126 upon the operator actuating control button 126. The actuation of the Hall-effect switch, corresponding to control button 126, causes the circuit board to provide appropriate signals to the function selection module and the input drive component of the drive mechanism to open/close end effector 400.

In addition, located immediately proximal to rocker device 130 is a respective Hall-effect switch (not shown) that is actuated upon the movement of a magnet (not shown) within rocker device 130 upon the operator actuating rocker device 130. The actuation of the Hall-effect switch, corresponding to rocker device 130, causes the circuit board to provide appropriate signals to the function selection module and the input drive component of the drive mechanism to rotate end effector 400 relative to shaft assembly 200 or rotate end effector 400 and shaft assembly 200 relative to instrument housing 102 of surgical instrument 100. Specifically, movement of rocker device 130 in a first direction causes end effector 400 and/or shaft assembly 200 to rotate relative to instrument housing 102 in a first direction, while movement of rocker device 130 in an opposite, e.g., second, direction causes end effector 400 and/or shaft assembly 200 to rotate relative to instrument housing 102 in an opposite, e.g., second, direction.

Turning now to FIGS. 1-29, shaft assembly 200 will be shown in detail and described. Shaft assembly 200 is configured to communicate the rotational forces of first, second and third rotatable drive members or connectors 118, 120, and 122 of surgical instrument 100 to end effector 400. As mentioned above, shaft assembly 200 is configured for selective connection to surgical instrument 100.

Figure 4:
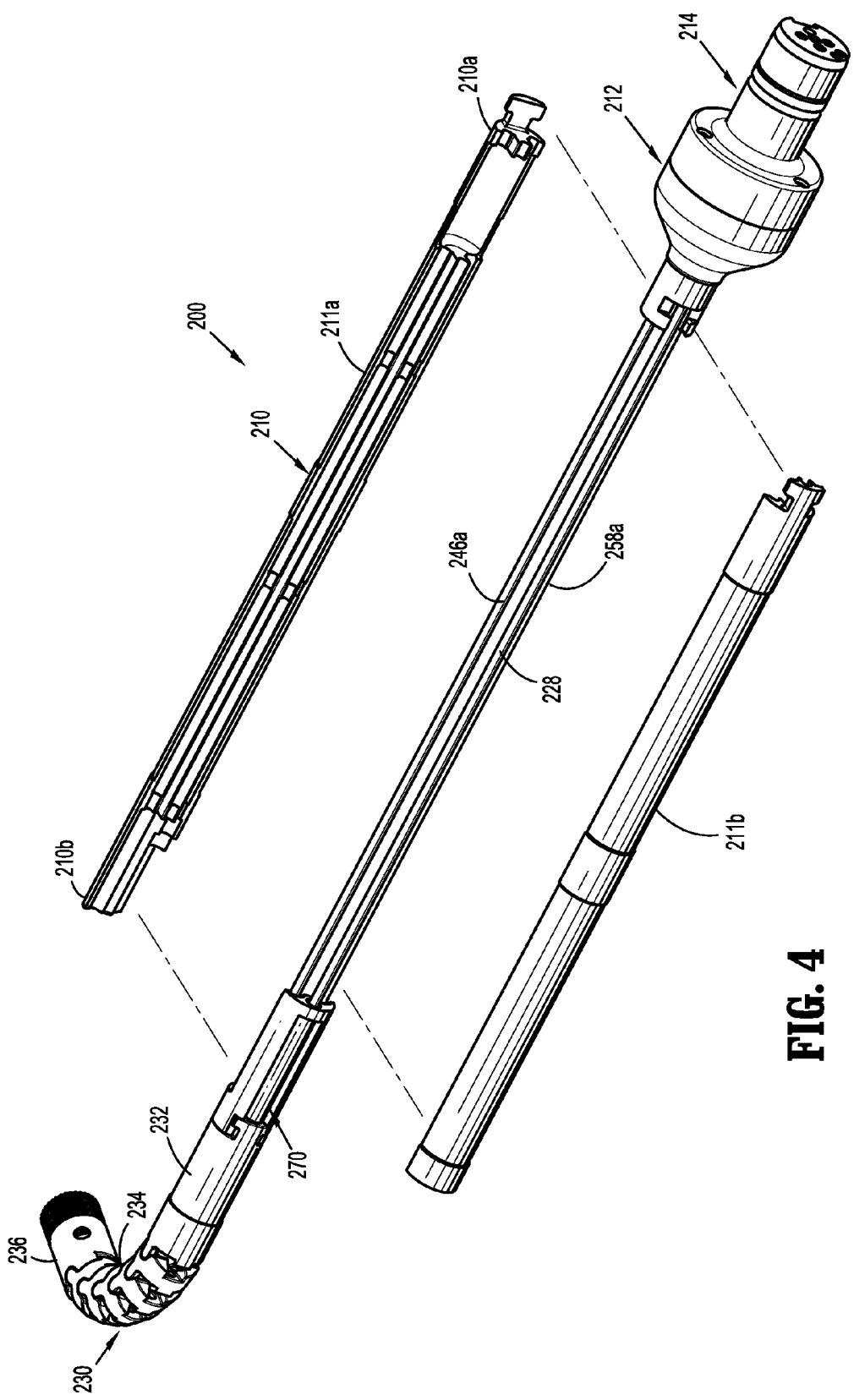
FIG. 4 is a perspective view, with parts separated, of the shaft assembly of FIGS. 1-3.

As seen in FIGS. 1, 2 and 4, shaft assembly 200 includes an elongate, substantially rigid, outer tubular body 210 having a proximal end 210a and a distal end 210b; a transmission housing 212 connected to proximal end 210a of tubular body 210 and being configured for selective connection to surgical instrument 100; and an articulating neck assembly 230 connected to distal end 210b of elongate body portion 210.

Transmission housing 212 is configured to house a pair of gear train systems therein for varying a speed/force of rotation (e.g., increase or decrease) of first, second and/or third rotatable drive members or connectors 118, 120, and/or 122 of surgical instrument 100 before transmission of such rotational speed/force to end effector 400.

Figure 5:
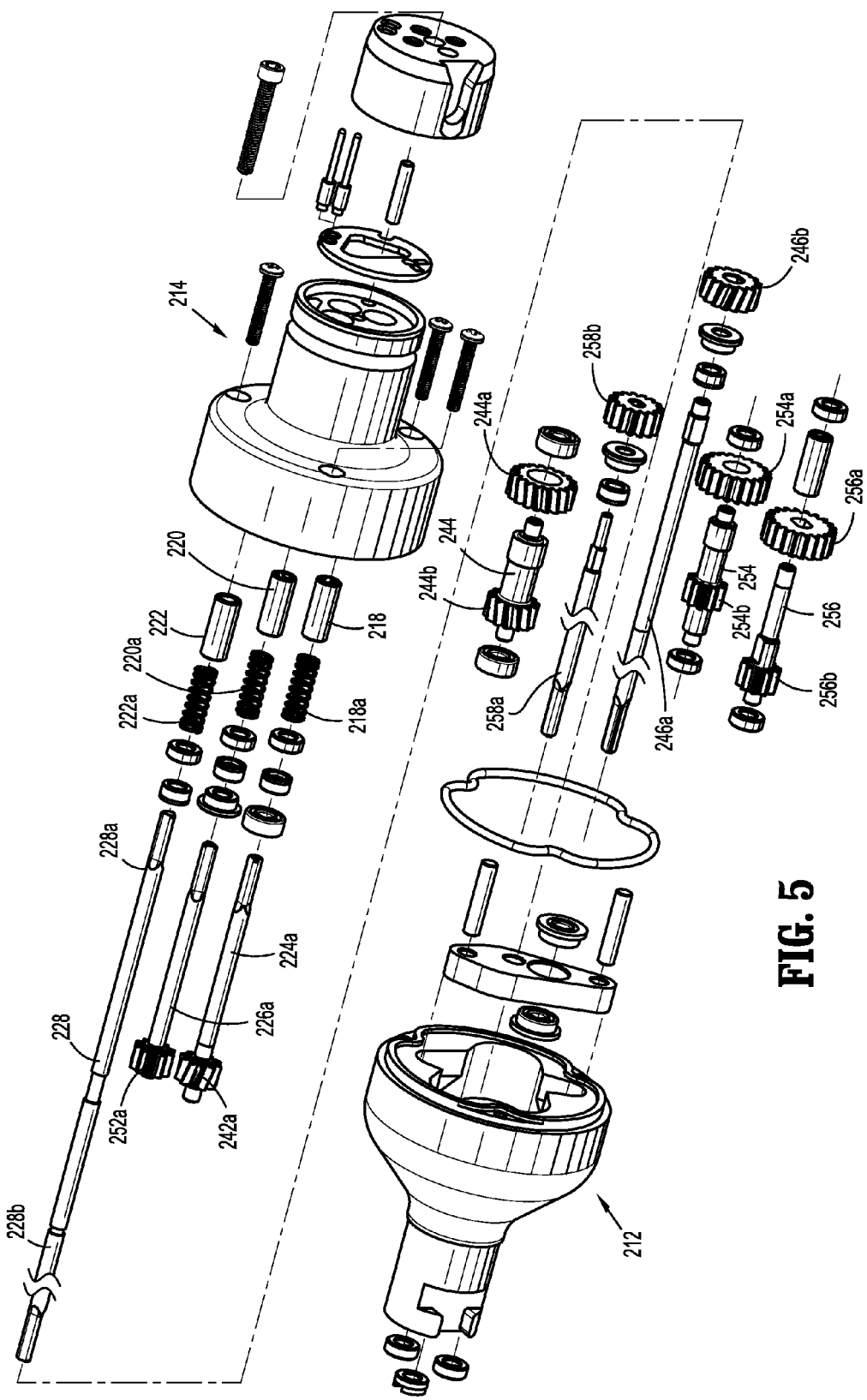
FIG. 5 is a perspective view, with parts separated of a transmission housing of the shaft assembly.

Transmission housing 212 of shaft assembly 200 is configured and adapted to connect to connecting portion 108a of upper housing portion 108 of surgical instrument 100. As seen in FIGS. 3-5, transmission housing 212 of shaft assembly 200 includes a shaft coupling assembly 214 supported at a proximal end thereof.

As seen in FIG. 5, transmission housing 212 and shaft coupling assembly 214 rotatably support a first proximal or input drive shaft 224a, a second proximal or input drive shaft 226a, and a third drive shaft 228.

Shaft coupling assembly 214 is configured to rotatably support first, second and third connector sleeves 218, 220 and 222, respectively. Each of connector sleeves 218, 220, 222 is configured to mate with respective first, second and third drive members or connectors 118, 120, 122 of surgical instrument 100, as described above. Each of connector sleeves 218, 220, 222 is further configured to mate with a proximal end of respective first input drive shaft 224a, second input drive shaft 226a, and third drive shaft 228.

Shaft drive coupling assembly 214 includes a first, a second and a third biasing member 218a, 220a and 222a disposed distally of respective first, second and third connector sleeves 218, 220, 222. Each of biasing members 218a, 220a and 222a is disposed about respective first proximal drive shaft 224a, second proximal drive shaft 226a, and third drive shaft 228. Biasing members 218a, 220a and 222a act on respective connector sleeves 218, 220 and 222 to help maintain connector sleeves 218, 220 and 222 engaged with the distal end of respective drive rotatable drive members or connectors 118, 120, 122 of surgical instrument 100 when shaft assembly 200 is connected to surgical instrument 100.

In particular, first, second and third biasing members 218a, 220a and 222a function to bias respective connector sleeves 218, 220 and 222 in a proximal direction. In this manner, during connection of shaft assembly 200 to surgical instrument 100, if first, second and or third connector sleeves 218, 220 and/or 222 is/are misaligned with the drive members or connectors 118, 120, 122 of surgical instrument 100, first, second and/or third biasing member(s) 218a, 220a and/or 222a are compressed. Thus, when the drive mechanism of surgical instrument 100 is engaged, drive members or connectors 118, 120, 122 of surgical instrument 100 will rotate and first, second and/or third biasing member(s) 218a, 220a and/or 222a will cause respective first, second and/or third connector sleeve(s) 218, 220 and/or 222 to slide back proximally, effectively coupling drive members or connectors 118, 120, 122 of surgical instrument 100 to respective first input drive shaft 224a, second input drive shaft 226a, and third drive shaft 228.

In use, during a calibration of surgical instrument 100, each of drive connectors 118, 120, 122 of surgical instrument 100 is rotated and the bias on connector sleeve(s) 218, 220 and 222 properly seats connector sleeve(s) 218, 220 and 222 over the respective drive connectors 118, 120, 122 of surgical instrument 100 when the proper alignment is reached.

Shaft assembly 200 includes a first and a second gear train system 240, 250, respectively, disposed within transmission housing 212 and tubular body 210, and adjacent coupling assembly 214. As mentioned above, each gear train system 240, 250 is configured and adapted to vary a speed/force of rotation (e.g., increase or decrease) of first and second rotatable drive connectors 118 and 120 of surgical instrument 100 before transmission of such rotational speed/force to end effector 400.

Figure 6:
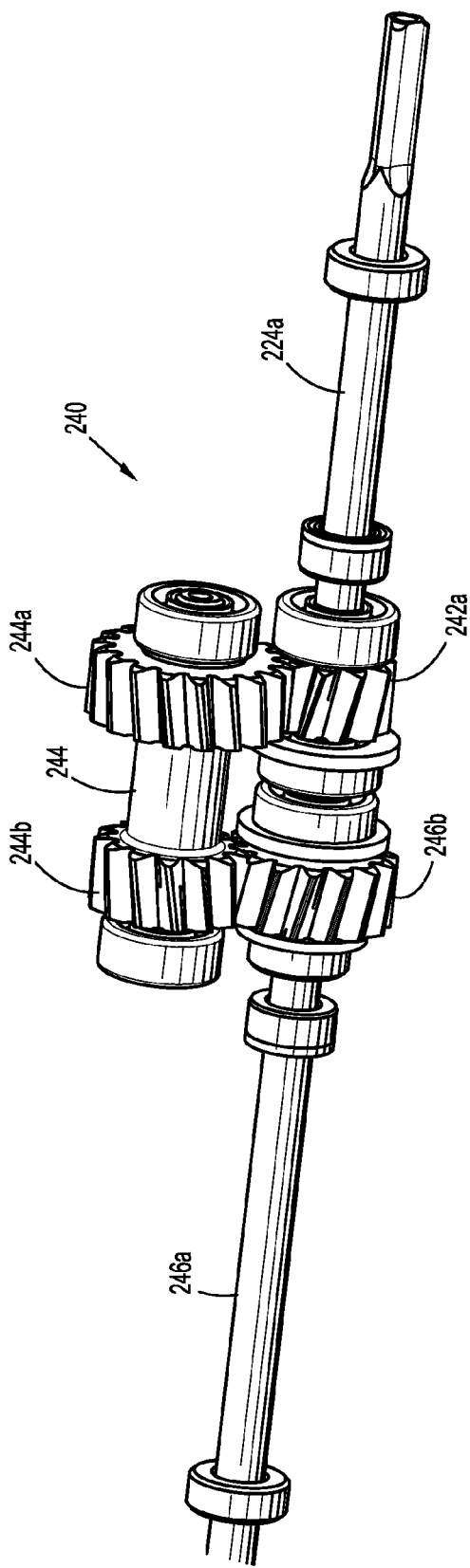
FIG. 6 is a perspective view of a first gear train system that is supported in the transmission housing.

As seen in FIGS. 5 and 6, first gear train system 240 includes first input drive shaft 224a, and a first input drive shaft spur gear 242a keyed to first input drive shaft 224a. First gear train system 240 also includes a first transmission shaft 244 rotatably supported in transmission housing 212, a first input transmission spur gear 244a keyed to first transmission shaft 244 and engaged with first input drive shaft spur gear 242a, and a first output transmission spur gear 244b keyed to first transmission shaft 244. First gear train system 240 further includes a first output drive shaft 246a rotatably supported in transmission housing 212 and tubular body 110, and a first output drive shaft spur gear 246b keyed to first output drive shaft 246a and engaged with first output transmission spur gear 244b.

In accordance with the present disclosure, first input drive shaft spur gear 242a includes 10 teeth; first input transmission spur gear 244a includes 18 teeth; first output transmission spur gear 244b includes 13 teeth; and first output drive shaft spur gear 246b includes 15 teeth. As so configured, an input rotation of first input drive shaft 224a is converted to an output rotation of first output drive shaft 246a by a ratio of 1:2.08.

As mentioned above, a proximal end of first input drive shaft 224a is configured to support first connector sleeve 218.

In operation, as first input drive shaft spur gear 242a is rotated, due to a rotation of first connector sleeve 258 and first input drive shaft 224a, as a result of the rotation of the first respective drive connector 118 of surgical instrument 100, first input drive shaft spur gear 242a engages first input transmission spur gear 244a causing first input transmission spur gear 244a to rotate. As first input transmission spur gear 244a rotates, first transmission shaft 244 is rotated and thus causes first output drive shaft spur gear 246b, that is keyed to first transmission shaft 244, to rotate. As first output drive shaft spur gear 246b rotates, since first output drive shaft spur gear 246b is engaged therewith, first output drive shaft spur gear 246b is also rotated. As first output drive shaft spur gear 246b rotates, since first output drive shaft spur gear 246b is keyed to first output drive shaft 246a, first output drive shaft 246a is rotated.

As will be discussed in greater detail below, shaft assembly 200, including first gear system 240, functions to transmit operative forces from surgical instrument 100 to end effector 400 in order to operate, actuate and/or fire end effector 400.

Figure 7:
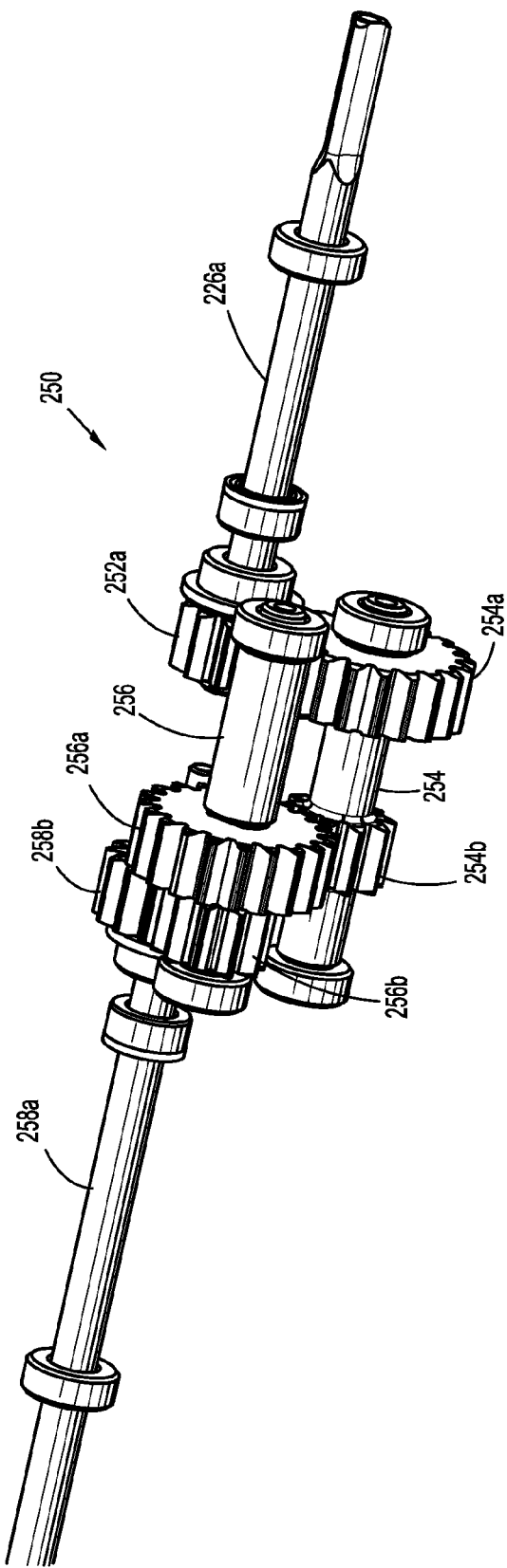
FIG. 7 is a perspective view of a second gear train system that is supported in the transmission housing.
Figure 8:
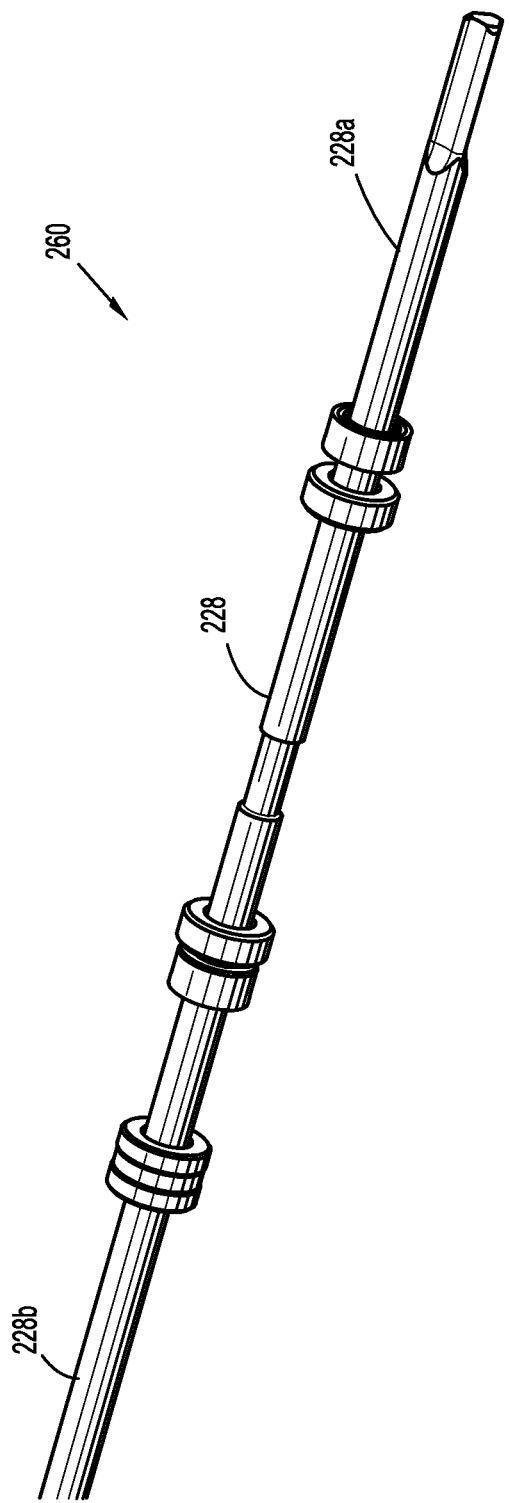
FIG. 8 is a perspective view of a third drive shaft that is supported in the transmission housing.
Figure 11:
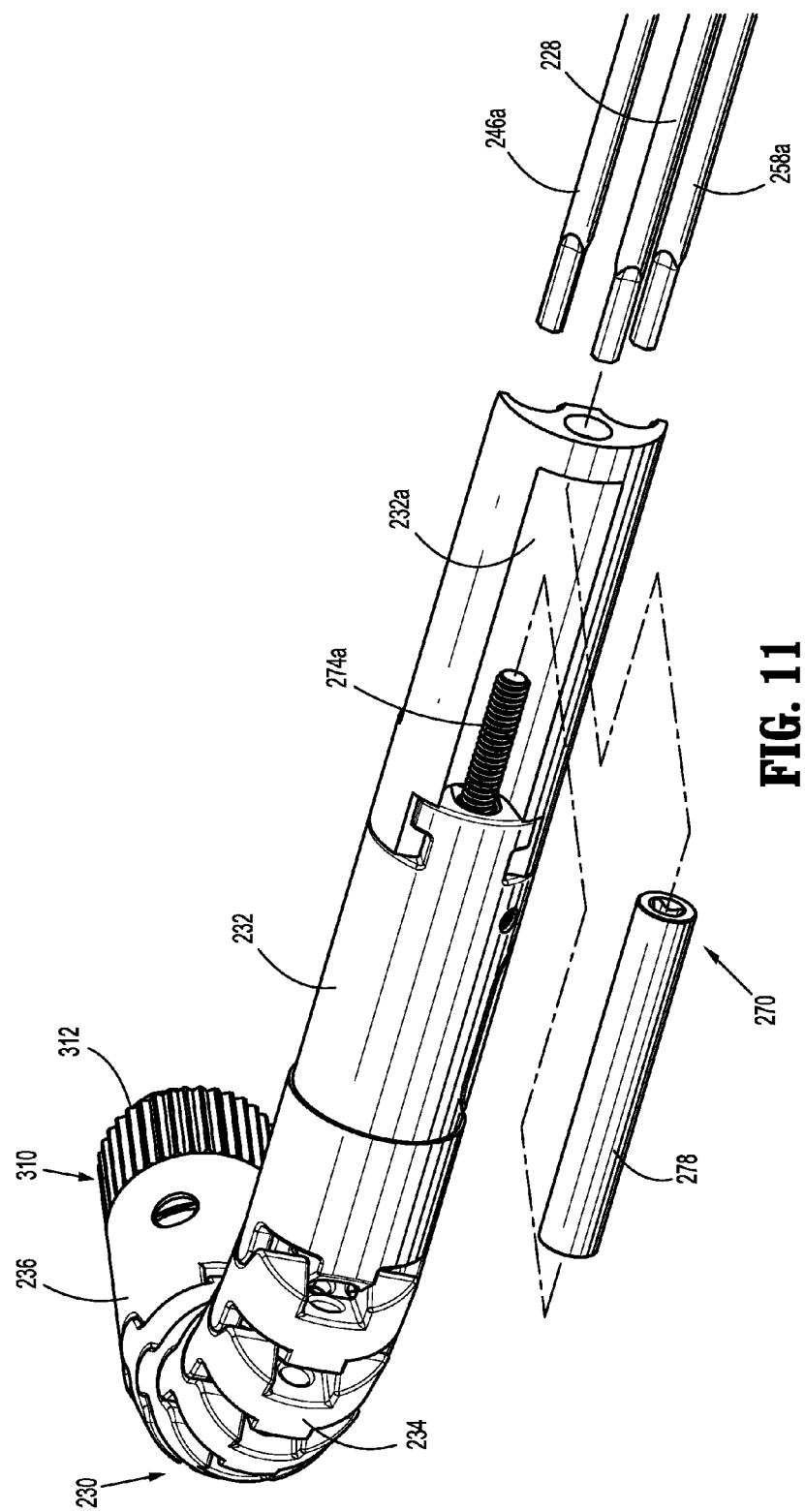
FIG. 11 is a perspective view of the neck assembly of FIGS. 9 and 10, with a threaded nut separated therefrom.

As seen in FIGS. 5 and 7, second gear train system 250 includes second input drive shaft 226a, and a second input drive shaft spur gear 252a keyed to second input drive shaft 226a. Second gear train system 250 also includes a first transmission shaft 254 rotatably supported in transmission housing 212, a first input transmission spur gear 254a keyed to first transmission shaft 254 and engaged with second input drive shaft spur gear 252a, and a first output transmission spur gear 254b keyed to first transmission shaft 254.

Second gear train system 250 further includes a second transmission shaft 256 rotatably supported in transmission housing 212, a second input transmission spur gear 256a keyed to second transmission shaft 256 and engaged with first output transmission spur gear 254b that is keyed to first transmission shaft 254, and a second output transmission spur gear 256b keyed to second transmission shaft 256.

Second gear train system 250 additionally includes a second output drive shaft 258a rotatably supported in transmission housing 212 and tubular body 210, and a second output drive shaft spur gear 258b keyed to second output drive shaft 258a and engaged with second output transmission spur gear 256b.

In accordance with the present disclosure, second input drive shaft spur gear 252a includes 10 teeth; first input transmission spur gear 254a includes 20 teeth; first output transmission spur gear 254b includes 10 teeth; second input transmission spur gear 256a includes 20 teeth; second output transmission spur gear 256b includes 10 teeth; and second output drive shaft spur gear 258b includes 15 teeth. As so configured, an input rotation of second input drive shaft 226a is converted to an output rotation of second output drive shaft 258a by a ratio of 1:6.

As mentioned above, a proximal end of second input drive shaft 226a is configured to support second connector sleeve 220.

In operation, as second input drive shaft spur gear 252a is rotated, due to a rotation of second connector sleeve 260 and second input drive shaft 226a, as a result of the rotation of the second respective drive connector 120 of surgical instrument 100, second input drive shaft spur gear 252a engages first input transmission spur gear 254a causing first input transmission spur gear 254a to rotate. As first input transmission spur gear 254a rotates, first transmission shaft 254 is rotated and thus causes first output transmission spur gear 254b, that is keyed to first transmission shaft 254, to rotate. As first output transmission spur gear 254b rotates, since second input transmission spur gear 256a is engaged therewith, second input transmission spur gear 256a is also rotated. As second input transmission spur gear 256a rotates, second transmission shaft 256 is rotated and thus causes second output transmission spur gear 256b, that is keyed to second transmission shaft 256, to rotate. As second output transmission spur gear 256b rotates, since second output drive shaft spur gear 258b is engaged therewith, second output drive shaft spur gear 258b is rotated. As second output drive shaft spur gear 258b rotates, since second output drive shaft spur gear 258b is keyed to second output drive shaft 258a, second output drive shaft 258a is rotated.

As will be discussed in greater detail below, shaft assembly 200, including second gear train system 250, functions to transmit operative forces from surgical instrument 100 to end effector 400 in order rotate shaft assembly 200 and/or end effector 400 relative to surgical instrument 100.

As mentioned above and as seen in FIGS. 5 and 8, transmission housing 212 and shaft coupling assembly 214 rotatably support a third drive shaft 228. Third drive shaft 228 includes a proximal end 228a configured to support third connector sleeve 222, and a distal end 228b extending to and operatively connected to an articulation assembly 270 as will be discussed in greater detail below.

As seen in FIG. 4, elongate, outer tubular body 210 of shaft assembly 200 includes a first half section 211a and a second half section 211b defining at least three longitudinally extending channels through outer tubular body 210 when half sections 211a, 211b are mated with one another. The channels are configured and dimensioned to rotatably receive and support first output drive shaft 246a, second output drive shaft 258a, and third drive shaft 228 as first output drive shaft 246a, second output drive shaft 258a, and third drive shaft 228 extend from transmission housing 212 to articulating neck assembly 230. Each of first output drive shaft 246a, second output drive shaft 258a, and third drive shaft 228 are elongate and sufficiently rigid to transmit rotational forces from transmission housing 220 to articulating neck assembly 230.

It is contemplated that the shaft assembly 200 can include channels therein, or exterior thereof, for transmitting fluids to the end effector. The fluids can be liquids or gases or other materials such as medicaments, hemostats, insufflation gas, irrigation fluid, etc.

Turning now to FIGS. 4 and 9-13, articulating neck assembly 230 is shown and described. Articulating neck assembly 230 includes a proximal neck housing 232, a plurality of links 234 connected to and extending in series from proximal neck housing 232; and a distal neck housing 236 connected to and extending from a distal-most link of the plurality of links 234.

Each link 234 includes cooperating knuckles and clevises formed on each of a proximal surface 234a and a distal surface 234b thereof. Proximal neck housing 232 includes knuckles and/or clevises that operatively engage with the knuckles and/or clevises of a proximal-most link. Distal neck housing 236 includes knuckles and/or devises that operatively engage with the knuckles and/or clevises of a distal-most link. The knuckles and clevises of adjacent neck housings 232, 236 and links 234 operatively engage with one another to define a direction and a degree of articulation of neck assembly 230.

Neck assembly 230 is configured to enable end effector 400 to move between a substantially linear configuration and a substantially angled, off-axis or articulated configuration. In accordance with the present disclosure, it is contemplated that neck assembly 230 is capable of articulating in a single plane and is capable of articulating approximately 90°, and even greater than 90°.

Figure 12:
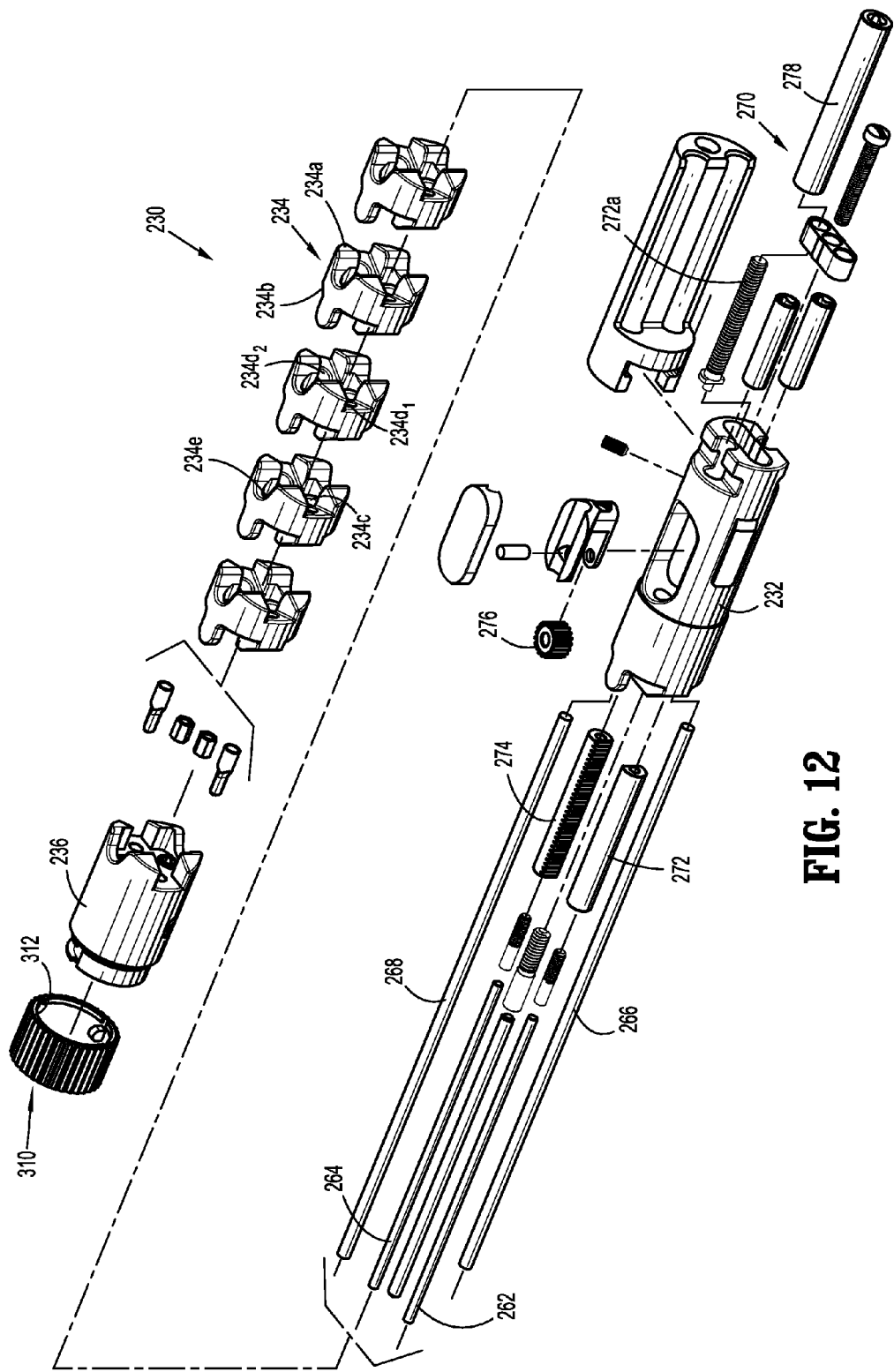
FIG. 12 is a perspective view, with parts separated, of the neck assembly of FIGS. 9-11.

Each link 234 defines a first lumen 234c (see FIG. 12) therein for passage of a first drive cable 266 therethrough; a first pair of opposed lumens $234d_1$, $234d_2$, for passage of a pair of articulation cables 262, 264 therethrough; and a second lumen 234e for passage of a second drive cable 268 therethrough. As seen in FIG. 12, first and second lumens 234c, 234e are diametrically opposed to one another and offset 90° relative to lumens $234d_1$, $234d_2$. Each of first drive cable 266 and second drive cable 268 includes a proximal end keyed to a distal end of respective first output drive shaft 246a and second output drive shaft 258a. Each of first and second drive cables 266, 268 is fabricated from a material that is both flexible and torsionally stiff (capable of transmitting rotational forces or torque), such as, for example, stainless steel and the like.

Figure 13:
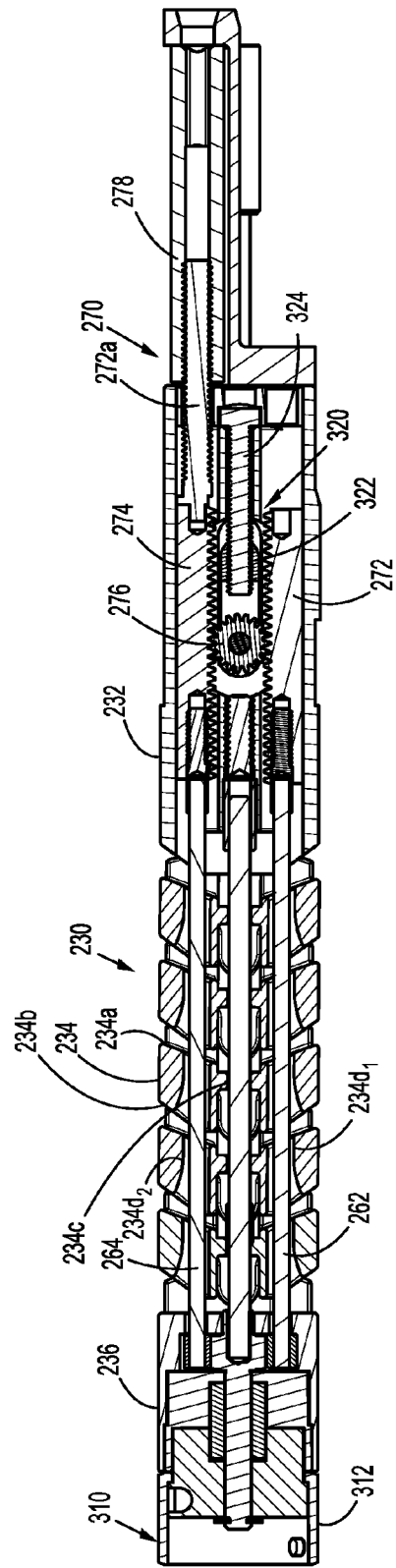
FIG. 13 is a cross-sectional view of the neck assembly of FIGS. 9-12, as taken through 13-13 of FIG. 9.
Figure 14:
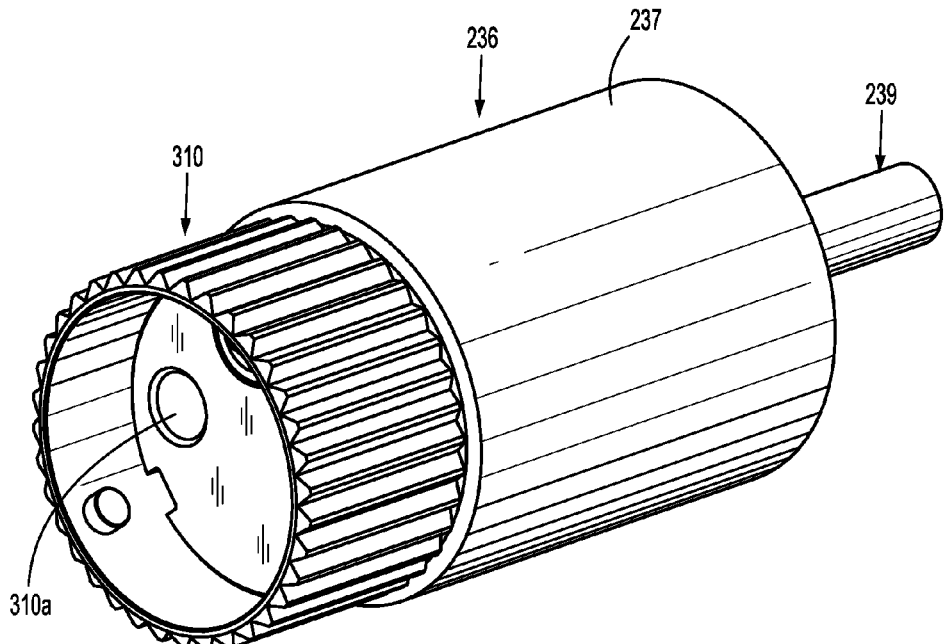
FIG. 14 an enlarged distal perspective view of a distal neck housing of the neck assembly of FIGS. 9-12.
Figure 15:
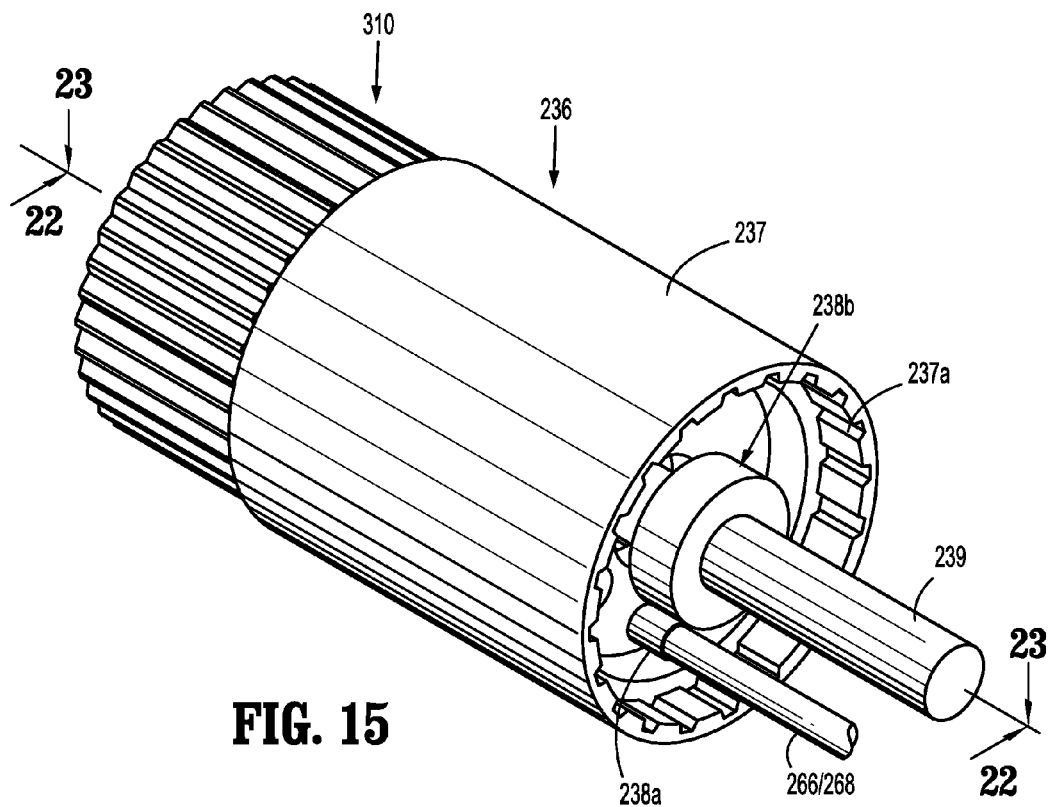
FIG. 15 is an enlarged proximal perspective view of the distal neck housing of FIG. 14.
Figure 16:
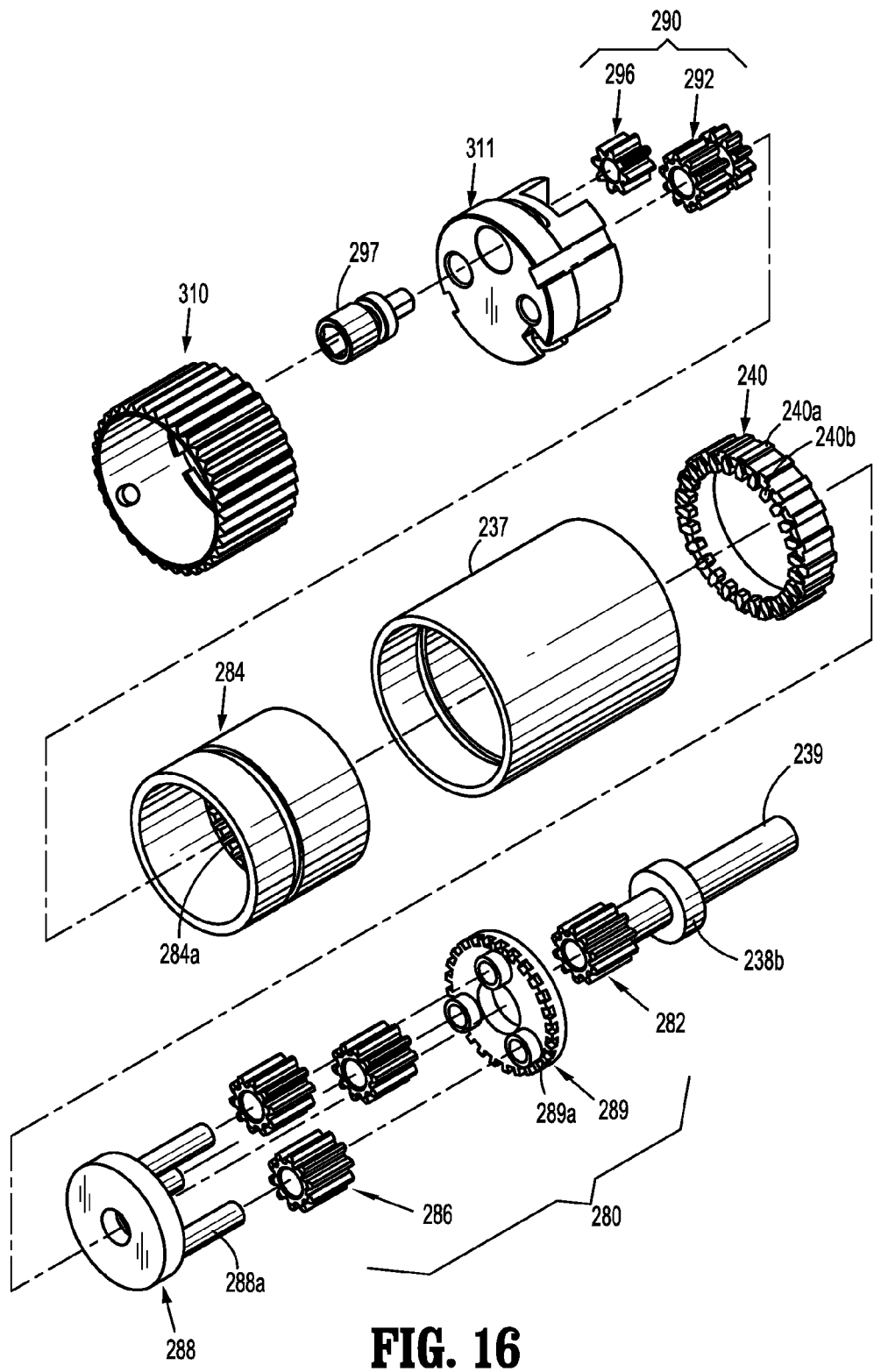
FIG. 16 is a perspective view, with parts separated, of the distal neck housing of FIGS. 14 and 15.
Figure 17:
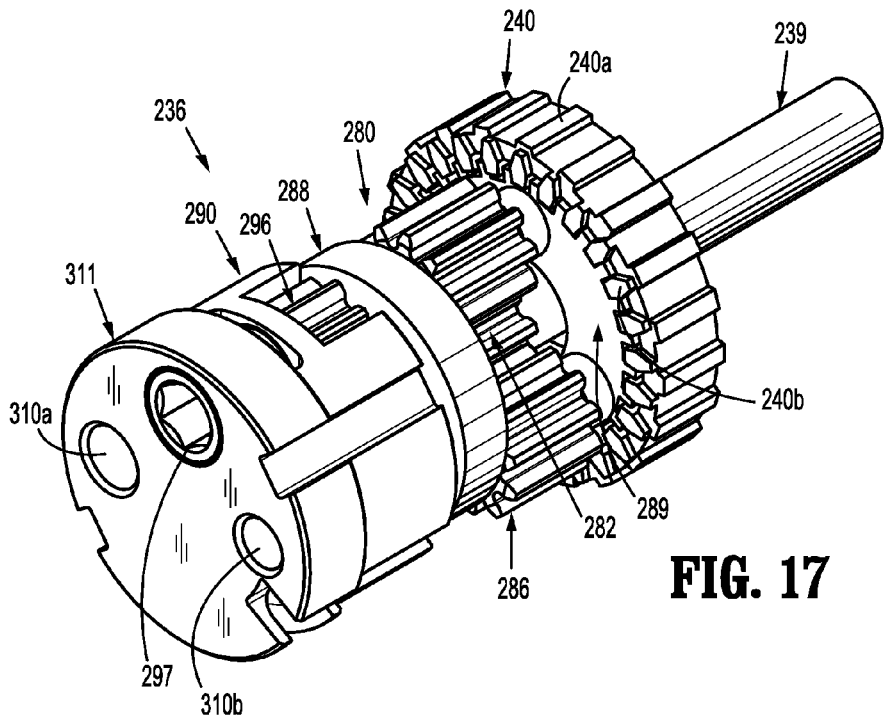
FIGS. 17 and 18 are perspective views of the distal neck housing of FIGS. 14-16, with an outer tubular housing removed therefrom.
Figure 18:
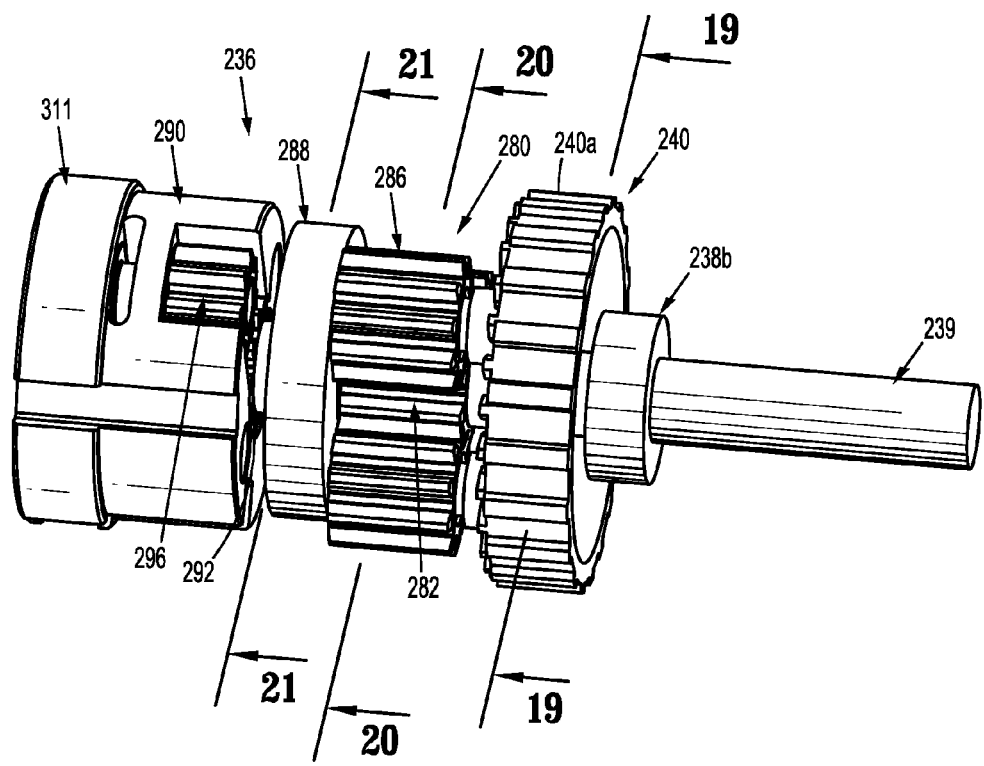
Figure 19:
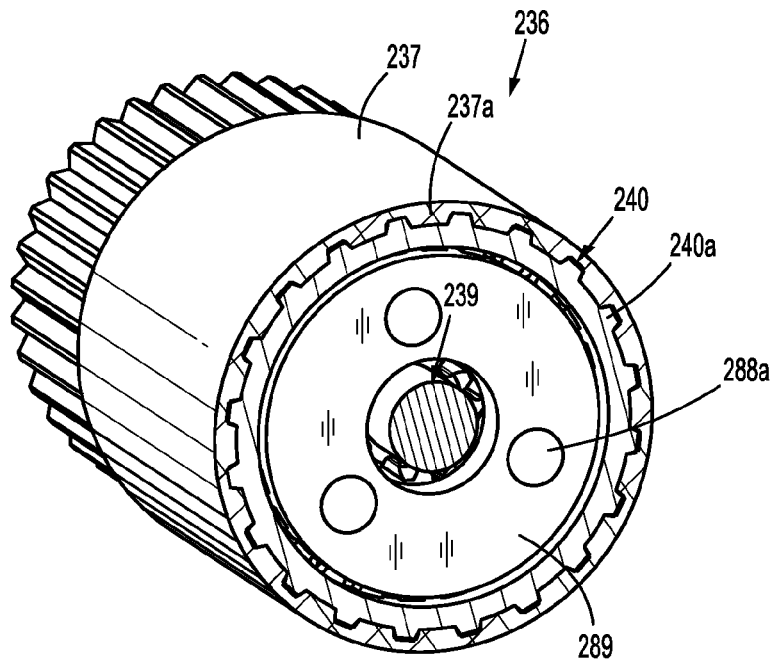
FIG. 19 is a cross-sectional view of the distal neck housing, as taken through 19-19 of FIG. 18.
Figure 20:
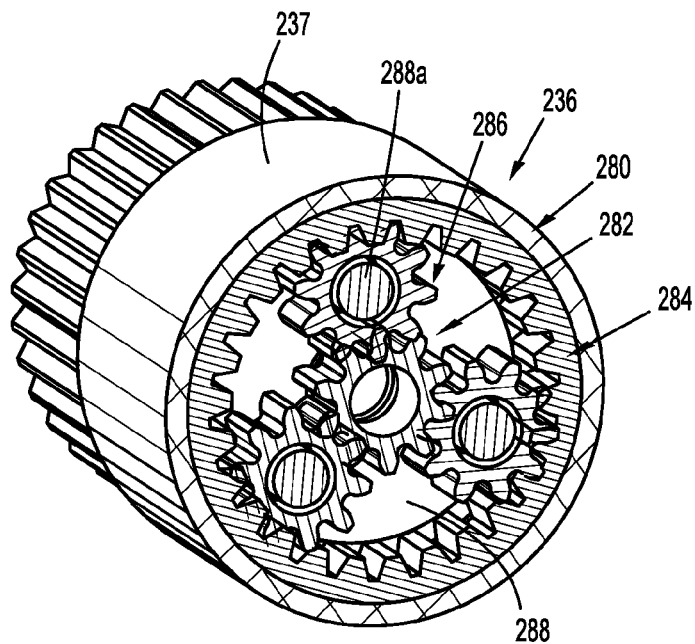
FIG. 20 is a cross-sectional view of the distal neck housing, as taken through 20-20 of FIG. 18.
Figure 21:
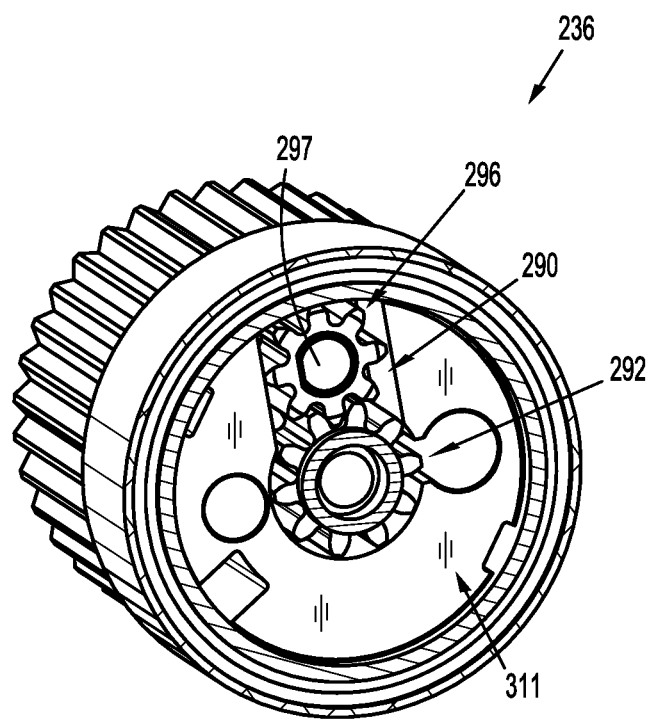
FIG. 21 is a cross-sectional view of the distal neck housing, as taken through 21-21 of FIG. 18.
Figure 22:
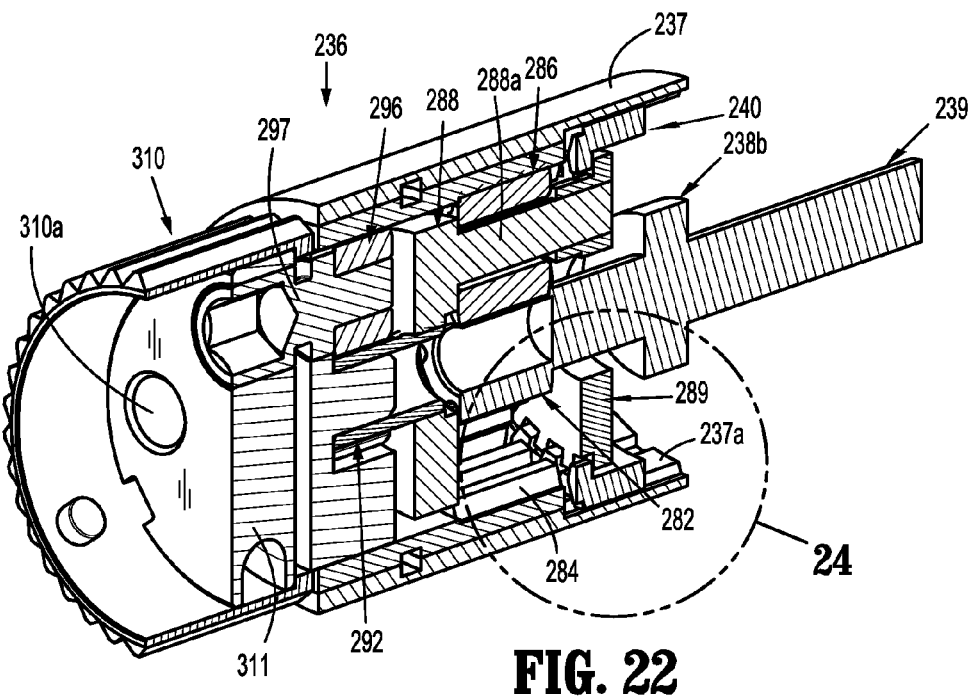
FIG. 22 is a cross-sectional view of the distal neck housing, as taken through 22-22 of FIG. 15, illustrating the distal neck housing in a rotation configuration.
Figure 23:
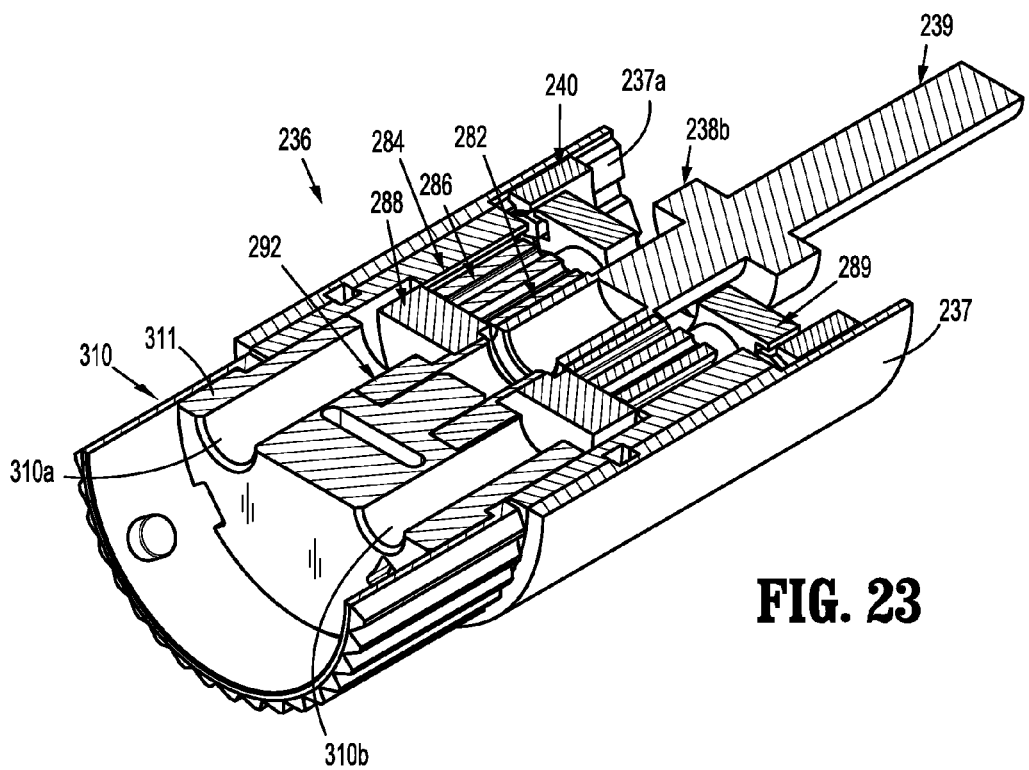
FIG. 23 is a cross-sectional view of the distal neck housing, as taken through 23-23 of FIG. 15, illustrating the distal neck housing in a rotation configuration.
Figure 24:
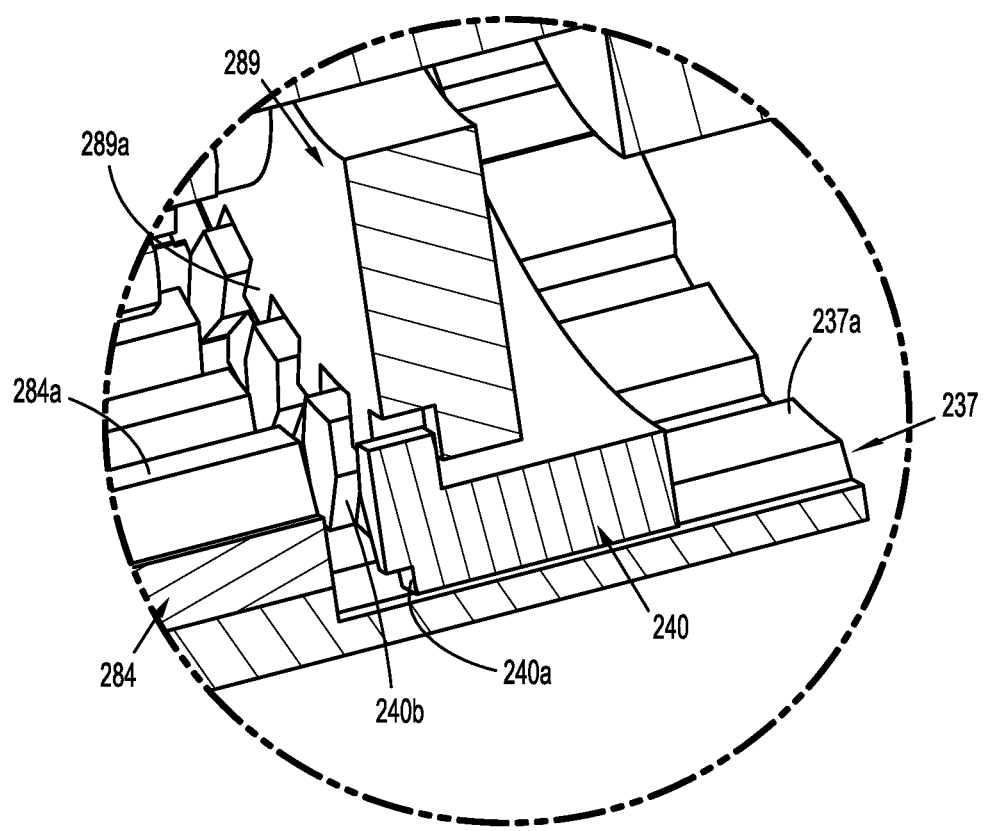
FIG. 24 is an enlarged view of the indicated area of detail of FIG. 22.

As seen in FIG. 13, proximal neck housing 232 of neck assembly 230 supports an articulation assembly 270 configured and adapted to impart articulation to neck assembly 230 and/or end effector 400. Articulation assembly 270 includes a pair of opposed gear racks 272, 274 engaged with and on opposed sides of a pinion gear 276. Racks 272, 274 are axially slidably supported in proximal neck housing 232 and pinion gear 276 is rotatably supported in proximal neck housing 232.

As seen in FIGS. 12 and 13, rack 274 is attached to a threaded shaft 272a extending proximally therefrom and that is in threaded engagement with a distal end of an internally threaded nut 278. Threaded nut 278 is rotatably supported and axially fixed within a pocket 232a formed in proximal neck housing 232. A proximal end of threaded nut 278 is keyed to a distal end of third drive shaft 228. While threaded shaft 272a is shown extending from rack 274, it is understood, and within the scope of the present disclosure, that the threaded shaft may extend from rack 272 without departing from the principles of the present disclosure.

Articulation cables 262, 264 include proximal ends that are secured to and extend from a respective distal end of racks 272, 274. Each articulation cable 262, 264 includes a distal end that extends through respective opposed lumens $234d_1$, $234d_2$ of links 234 and that is secured to or anchored in distal neck housing 234.

In operation, to articulate neck assembly 230 in a first direction, third drive shaft 228 is rotated in a first direction, as described above, to rotate threaded nut 278 and axially displace threaded shaft 272a distally to axially displace rack 274 distally. As rack 274 is displaced axially, in a distal direction, rack 274 causes pinion gear 276 to be rotated and to thus act on rack 272, to axially displace rack 272 in a proximal direction. As rack 272 is axially displaced in a proximal direction, rack 272 causes articulation cable 262 to be drawn in a proximal direction and thereby articulate neck assembly 230. Neck assembly 230 is permitted to articulate since axially displacement of rack 274, in a distal direction, results in axial, distal displacement of articulation cable 264.

Turning now to FIGS. 14-29, distal neck housing 236 functions as a gear box and supports a first or proximal planetary gear system 280 and a second or distal planetary gear system 290. First planetary gear system 280 and the distal gear system 290 function in cooperation with one another to transmit a rotation of one of first drive cable 266 or second drive cable 268 to end effector 400 to effectuate both a firing of end effector 400 and a rotation of end effector 400. In other words, first or proximal planetary gear system 280 and a second or distal planetary gear system 290 are configured to convert a rotational input of a single rotatable drive member (i.e., first drive cable 266, second drive cable 268) into at least two output forces to end effector 400, a first output force effectuating a firing of end effector 400, and a second output force effectuating a rotation of end effector 400. Thus, one drive shaft can drive or actuate more than one function.

Distal neck housing 236 includes an outer tubular housing 237 defining a set of radial gear teeth 237a on an inner surface thereof, near a proximal end thereof.

In particular, a distal end of either first drive cable 266 or a distal end of second drive cable 268 selectively engages a first spur gear 238a supported on distal neck housing 236. First spur gear 238a is in engagement with a second spur gear 238b that is non-rotatably supported on a central distal drive shaft 239, wherein distal drive shaft 239 is rotatably supported in distal neck housing 236.

As seen in FIGS. 16-20 and 22-26, first planetary gear system 280 of distal neck housing 236 includes a first sun gear 282 non-rotatably supported on distal drive shaft 239, a first ring gear 284 surrounding first sun gear 282, and a plurality of first planet gears 286 interposed between and inter-engaging first spur gear 282 and first ring gear 284. The plurality of first planet gears 286 are rotatably supported on respective stems 288a of a carrier 288. Carrier 288 is rotatably supported in distal neck housing 236. Carrier 288 non-rotatably supports a crown gear 289 on stems 288a, such that rotation of crown gear 289 results in rotation of carrier 288 and first planet gears 286. Crown gear 289 defines a plurality of teeth 289a radially around an outer rim thereof, wherein teeth 289a extend only through or from a distal surface of crown gear 289.

As seen in FIGS. 16-18 and 21-26, distal gear system 290 of distal neck housing 236 includes a second sun gear 292 non-rotatably supported on and extending from carrier 288 and at least one second planet gear 296 engaged with second sun gear 292. In an embodiment, it is contemplated that an annular flange extends from first ring gear 284 to extend distally beyond second planetary gear system 290 to non-rotatably engage a rotation hub 311 of an end effector coupling assembly 310 such that rotation of first ring gear 284 results in rotation of hub 311 of end effector coupling assembly 310.

Turning back to FIGS. 16-20 and 22-26, distal neck housing 236 supports a lock collar gear 240 thereon. Lock collar gear 240 is supported on distal neck housing 236 and includes a plurality of radially outward extending teeth 240a (in the form of a spur gear) engaged with the teeth 237a of tubular housing 237, and a plurality of distally facing teeth 240b (in the form of a crown gear) that extend radially inward of an inner-most surface of lock collar gear 240. Lock collar gear 240 is non-rotatably slidable, relative to crown gear 289, between a proximal position, engaged with crown gear 289 of first planetary gear system 280, and a distal position, disengaged from crown gear 289.

In operation, when lock collar gear 240 is in the proximal engaged position with crown gear 289, as seen in FIGS. 17, 18 and 22-24, distally facing and inwardly projecting teeth 240b thereof engage with crown teeth 289a of crown gear 289, such that crown gear 289 and carrier 288 are prevented from rotating due to radially outward extending teeth 240a of lock collar gear 240 being engaged with teeth 237a of tubular housing 237.

Figure 25:
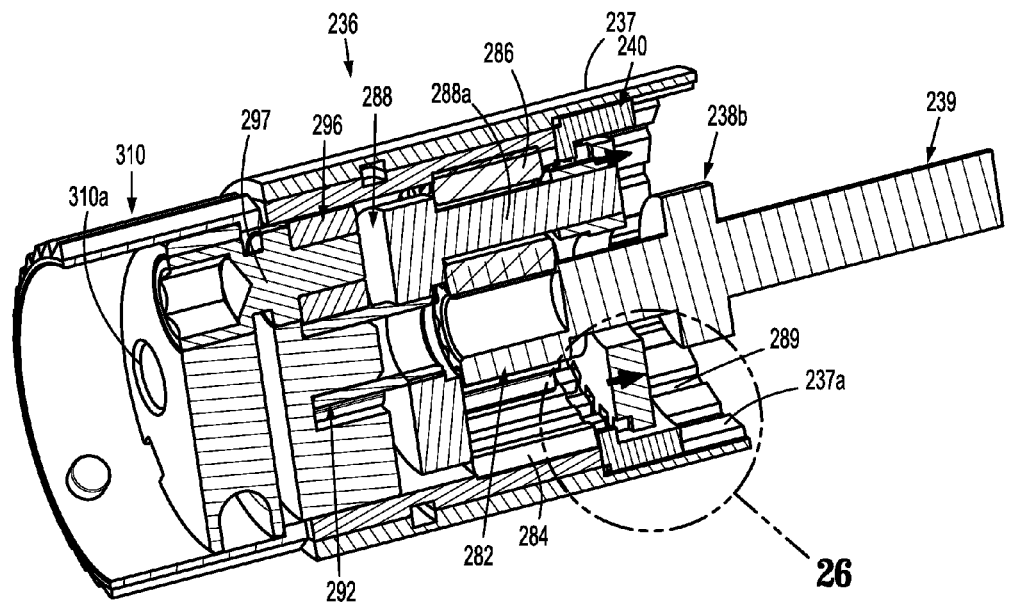
FIG. 25 is a cross-sectional view of the distal neck housing, as taken through 22-22 of FIG. 15, illustrating the distal neck housing in a firing configuration.
Figure 26:
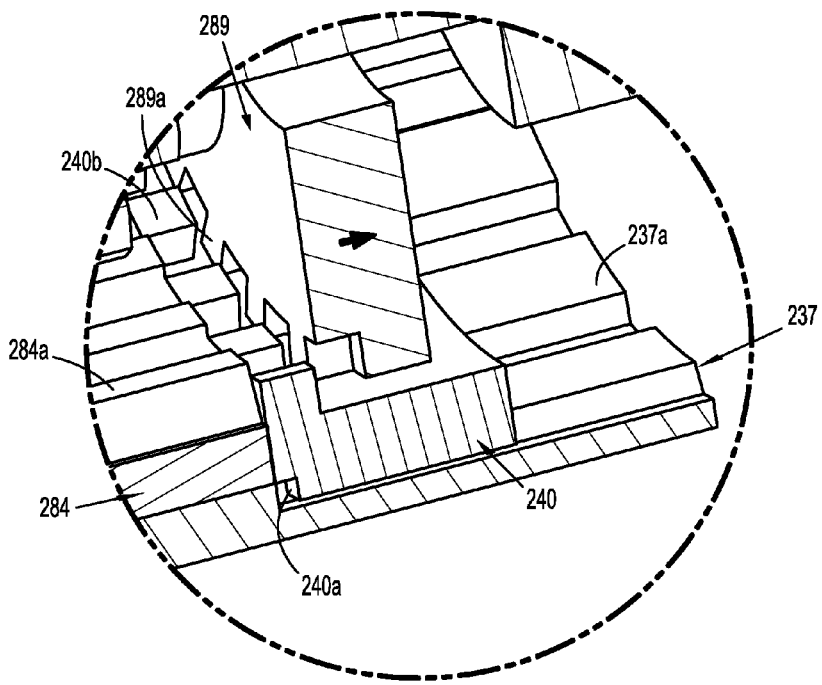
FIG. 26 is an enlarged view of the indicated area of detail of FIG. 25.

Also in operation, when lock collar gear 240 is in the distal disengaged position with crown gear 289, as seen in FIGS. 25 and 26, distally facing and inwardly projecting teeth 240b thereof are disengaged from crown teeth 289a of crown gear 289, such that crown gear 289 and carrier 288 rotate due to a rotation of spur gear 282. With lock collar gear 240 disengaged from crown gear 289, crown gear 289, and thus carrier 288, are permitted to rotate.

In an overall operation, as either first drive cable 266 or second drive cable 268 is rotated, due to a rotation of first output drive shaft 246a or second output drive shaft 258a (as described above), as seen in FIGS. 15-21, said rotation is transmitted to first spur gear 238a of distal neck housing 236. As first spur gear 238a is rotated, said rotation is transmitted to second spur gear 238b that is non-rotatably supported on central distal drive shaft 239 to transmit rotation to central distal drive shaft 239.

Depending on a positioning of lock collar gear 240, relative to crown gear 289 of first planetary gear system 280, rotation of central distal drive shaft 239 will result in either a closing/firing and opening/retraction of end effector 400, or a rotation of end effector 400. For example, in an embodiment, when lock collar gear 240 is located in a distal position, disengaged from crown gear 289 (as described above and shown in FIGS. 25 and 26), rotation of central distal drive shaft 239 will result in a closing/firing and opening/retraction of end effector 400. Moreover, in an embodiment, when lock collar gear 240 is located in a proximal position, engaged with crown gear 289 (as described above and shown in FIGS. 17, 18 and 22-24), rotation of central distal drive shaft 239 will result in a rotation of end effector 400.

Continuing with a discussion of the operation, in order to rotate end effector 400, as seen in FIGS. 17, 18 and 22-24, lock collar gear 240 is moved to the proximal position to engage crown gear 289, and since crown gear 289 is non-rotatably connected to carrier 288 via stems 288a, non-rotation of carrier 288 results in non-rotation of crown gear 289. Thus, with crown gear 289 incapable of rotating, rotation of central distal drive shaft 239 is transmitted to and results in rotation of first sun gear 282 and, in turn, rotation of the plurality of first planet gears 286 about their respective central axes defined by stems 288a of carrier 288. As first planet gears 286 are rotated about their respective central axes defined by stems 288a of carrier 288, first planet gears 286 transmit said rotation to first ring gear 284.

As first ring gear 284 is rotated, first ring gear 284, being non-rotatably connected to tubular housing 237, transmits said rotation to tubular housing 237 and/or rotation hub 311 supported in distal neck housing 236. In an embodiment, as tubular housing 237 is rotated, tubular housing 237 may transmit said rotation to rotation hub 311 supported in distal neck housing 236. Thus, when end effector 400 is connected to shaft assembly 200, and specifically, when alignment stems 424a, 424b of end effector 400 (see FIGS. 29 and 30) are connected to rotation hub 311, a rotation of rotation hub 311 results in rotation of end effector 400.

Continuing with a discussion of the operation, in order to close/fire and open/retract end effector 400, as seen in FIGS. 25 and 26, lock collar gear 240 is moved to the distal position to be disengaged from carrier 288 and permit crown gear 289 to rotate. Thus, with crown gear 289 permitted to rotate, rotation of central distal drive shaft 239 results in rotation of carrier 288.

As carrier 288 is rotated, carrier 288 transmits said rotation to second sun gear 292 of distal gear system 290. As second sun gear 292 is rotated, second sun gear 292 transmits said rotation to the at least one second gear 296. As the second gear 296 is rotated, the second gear 296 transmits said rotation to a firing connector 297 which is configured to selective engage with a drive axle 426 (see FIGS. 27, 29 and 30) of end effector 400 to thereby effectuate a firing and a closing of end effector 400.

In accordance with an embodiment of the present disclosure, it is contemplated that lock collar gear 240 is biased to the proximal position, wherein lock collar gear 240 is engaged with crown gear 289. Such an arrangement acts as a failsafe, wherein shaft assembly 200 will default to a fire (or retract) mode. It is contemplated that distal neck housing 236 may include a biasing member 244 positioned so as to act on lock collar gear 240 and urge lock collar gear 240 to the proximal position.

In accordance with an embodiment of the present disclosure, it is contemplated that shaft assembly 200 may include a shift cable 246 having a first end attached to lock collar gear 240 and a second end extending through shaft assembly 200 to be accessible from a location external of an operative field or operative cavity. It is contemplated that shift cable 246 may also be biased to a distal position. In an embodiment, the spring rate/constant of the biasing member associated with shift cable 246 is greater than a spring rate/constant of biasing member 244 associated with lock collar gear 240.

As so configured, shift cable 246 is capable of being pulled completely (moved proximally), even if the teeth 240b of lock collar gear 240 are aligned with the teeth 289a of crown gear 289 thus preventing engagement, the biasing member associated with shift cable 246 will hold lock collar gear 240 against crown gear 289 until distal drive shaft 239 of distal neck housing 236 is rotated, in which the torque will rotate first sun gear 282 and crown gear 289, thereby permitting the teeth 240b of lock collar gear 240 to en-mesh with the teeth 289a of crown gear 289.

The reverse occurs when shift cable 246 is released from a proximal position. With lock collar gear 240 spring loaded towards crown gear 289, even if the teeth of lock collar gear 240 are aligned with the teeth of crown 289 thus preventing engagement, biasing member 242 will hold lock collar gear 240 against crown gear 289 until distal drive shaft 239 of distal neck housing 236 is rotated, in which the torque will rotate first sun gear 282 and crown gear 289, thereby permitting the teeth of lock collar gear 240 to en-mesh with the teeth of crown gear 289.

By providing first and second gear systems 280, 290 in distal neck housing 236 (at a location between articulating neck assembly 230 and end effector 400), only a single rotatable drive is required to be driven/rotated through articulating neck assembly 230. Additionally, the use of first and second planetary gear systems permits a greater torque reduction in an axially shorter assembly as compared to a gear system made up of a series of compound gears.

As seen in FIGS. 14, 15 and 27-29, shaft assembly 200 further includes an end effector coupling assembly 310 supported at a distal end of distal neck housing 236 of articulating neck assembly 230. End effector coupling assembly 310 includes a collar 312 rotatably supported on and extending distally from distal neck housing 236 and being biased to a first radial portion. Collar 312 is rotatable from a first radial position to a second radial position, wherein end effector 400 is matable to end effector coupling assembly 310, and returns, by way of the bias, to the first radial position, to lock end effector 400 to shaft assembly 200.

Figure 30:
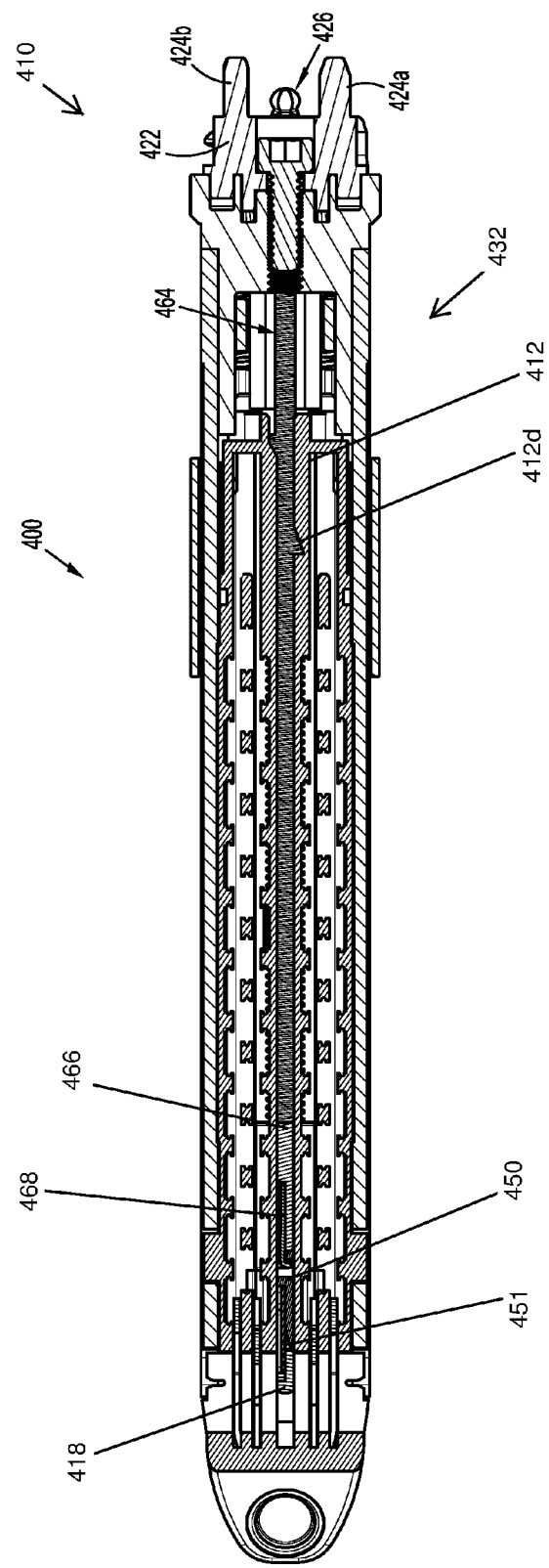
FIG. 30 is a cross-sectional view of the end effector, as taken through 30-30 of FIG. 27.

With reference to FIG. 30, end effector 400 includes an actuation sled 418 and a knife sled 450 proximal of actuation sled 418. Knife sled 450 includes a lock-out spring 451 extending distally therefrom for engaging a lock-out notch 412d formed in a surface of a cartridge body 412 of end effector 400. Lock-out spring 451 is biased toward lock-out notch 412d. Prior to firing of cartridge assembly 410, with actuation sled 418 and knife sled 450 at a proximal-most position in cartridge body 412, lock-out spring 451 is blocked by actuation sled 418 from entering lock-out notch 412d of cartridge body 412.

End effector 400 further includes a drive beam 466, disposed proximally of knife sled 450, and coupled to drive screw 464. Drive beam 466 includes a lock clip 468 extending distally therefrom. Lock clip 468 is configured to engage knife sled 450 and is biased to extend away from knife sled 450. Prior to firing the cartridge assembly 410, the drive beam 466 is at a proximal-most position in lower jaw 432 and actuation sled 418 and knife sled 450 are at a proximal-most position in cartridge body 412. Lock clip 468, prior to firing, is disengaged from knife sled 450. As drive beam 466 is advanced distally, lock clip 468 is cammed by cartridge body 412 into engagement with knife sled 450. After a complete or partial firing, drive screw 464 is rotated, such that drive beam 466 is retracted, thereby retracting knife sled 450 engaged to drive beam 466 via lock clip 468.

It is contemplated that collar 312 includes at least one nub 312a extending radially inward from inner surface thereof for receipt in a respective complementary structure 422a formed in an outer surface of end effector 400 to connect end effector 400 to shaft assembly 200 in the manner of a bayonet-type connection. Other forms of connection are contemplated, such as, detents, threaded connections, bayonet, etc.

Turning now to FIGS. 27-30, an exemplary end effector 400, for use with surgical instrument 100 and shaft assembly 200 is shown. Reference may be made to U.S. patent application Ser. No. 13/280,898, filed on Oct. 25, 2011, and U.S. patent application Ser. No. 13/280,859, filed Oct. 25, 2011, the entire contents of each of which is hereby incorporated by reference herein in their entirety. These applications have a detailed discussion of the construction and operation of exemplary end effectors. As seen in FIGS. 27-30, end effector assembly 400 includes a drive axle 426 rotatably supported and projecting proximally from coupling member 422 and being configured for mating engagement with firing connector 297 of distal neck housing 236, when end effector 400 is coupled to shaft assembly 200. Drive axle 426 functions to transmit rotational drive forces from firing connector 297 of distal neck housing 236 of shaft assembly 200, to a drive screw 464 of a lower jaw of the jaw assembly of end effector 400.

As seen in FIGS. 27-30, coupling member 422 includes a pair of spaced apart alignment stems 424a, 424b projecting proximally therefrom, for receipt in respective alignment bores 310a, 310b formed in a distal surface of end effector coupling assembly 310.

It will be understood that various modifications may be made to the embodiments disclosed herein. For example, surgical instrument 100 and/or cartridge assembly 410 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed is:

1. An electromechanical surgical system, comprising:
a hand-held surgical instrument including an instrument housing defining a connecting portion for selectively connecting with a shaft assembly, the surgical instrument having at least one rotatable drive member;
an end effector configured to perform at least one function;
the shaft assembly being arranged for selectively interconnecting the end effector and the surgical device, the shaft assembly including:
a transmission housing configured and adapted for selective connection to the connecting portion of the surgical device and to be in operative communication with each of the at least one rotatable drive member of the surgical device;
an outer tubular body having a proximal end supported by the transmission housing and a distal end configured and adapted for operative connection with the end effector;
a distal neck housing for interconnecting a rotatable drive member of the surgical instrument and a rotation receiving member supported in the end effector, wherein the distal neck housing includes a first end that is connectable to one rotatable drive member of the surgical instrument and a second end that is connectable to the rotation receiving member of the end effector, wherein the distal neck housing transmits a rotation of the rotatable drive member of the surgical instrument to the rotation receiving member of the end effector, the distal neck housing including:
at least one gear system configured to convert a rotational input of the rotatable drive member into at least two output forces to the end effector, wherein a first output force of the at least one gear system of the distal neck housing results in a firing of the end effector or a rotation of the end effector relative to the shaft assembly;
a lock collar non-rotatably and slidably supported on the distal neck housing, the lock collar movable between a first position wherein the first output force of the at least one gear system of the distal neck housing results in the firing of the end effector, and a second position wherein the first output force of the at least one gear system of the distal neck housing results in the rotation of the end effector relative to the shaft assembly; and
an articulating neck assembly interconnecting the tubular body and the distal neck housing, wherein the articulating neck assembly is configured to enable off-axis articulation of the distal neck assembly, and wherein the rotatable drive member extends through the articulating neck assembly.

2. The electromechanical surgical system according to claim 1, wherein the distal neck housing includes:
- an outer tubular housing defining at least one tooth extending radially inward therefrom; and
- a first planetary gear system supported in the outer tubular housing, the first planetary gear system includes:
  - a first sun gear drivable by the one rotatable drive member of the surgical instrument;
  - a ring gear rotatably supported in the outer tubular housing;
  - at least one first planet gear interposed and inter-engaging the first sun gear and the ring gear; and
  - a carrier rotatably supported in the outer tubular housing, the carrier including a respective stem rotatably supporting each first planet gear;
- wherein when the first sun gear rotates each first planet gear about an axis of rotation of first sun gear, the end effector is fired; and
- wherein when the first sun gear rotates each first planet gear about a respective axis of rotation, the end effector is rotated.

3. The electromechanical surgical system according to claim 2, wherein the distal neck housing further includes:
- a crown gear non-rotatably connected to the carrier; and
- a lock collar gear axially, non-rotatably and slidably supported in the outer tubular housing,
- wherein the lock collar gear includes a first position wherein the lock collar gear engages the crown gear and prevents the crown gear from rotating, wherein non-rotation of the crown gear permits the rotation of the end effector, and
- wherein the lock collar gear includes a second position wherein the lock collar gear is disengaged from the crown gear and permits the crown gear to rotating, wherein rotation of the crown gear permits the firing of the end effector.

4. The electromechanical surgical system according to claim 3, wherein the distal neck housing further includes:
- a rotation hub non-rotatably supported in outer tubular housing; and
- a second planetary gear system supported in the rotation hub, the second planetary gear system includes:
  - a second sun gear non-rotatably connected to the carrier; and
  - at least one second planet gear rotatably supported in the rotation hub and inter-engaged with the second sun gear; and
  - a firing connector connected to one of the at least one second planet gear, wherein the firing connector is configured to engage a force receiving member of the end effector;
- wherein when the carrier rotates, the second sun gear is rotated to rotate the at least one second planet gear and to fire the end effector.

5. The electromechanical surgical system according to claim 1, wherein the hand-held surgical instrument further includes:
- at least one drive motor supported in the instrument housing and being configured to rotate the at least one rotatable drive member;
- a battery disposed within the instrument housing for powering the at least one drive motor; and
- a circuit board disposed within the instrument housing for controlling power delivered from the battery to the motor.

6. The electromechanical surgical system according to claim 5, wherein the end effector includes:

- an upper jaw and a lower jaw, at least one of the upper jaw and the lower jaw being movable in relation to the other of the upper jaw and the lower jaw;
- a cartridge assembly supported in the lower jaw, the cartridge assembly including a plurality of staples therein;
- at least one surgical buttress releasably secured to a tissue contacting surface of at least one of the upper jaw and the lower jaw, the at least one surgical buttress secured to the at least one of the upper jaw and the lower jaw by at least one suture, the at least one of the upper jaw and the lower jaw being configured to receive a portion of the at least one suture.

7. The electromechanical surgical system according to claim 6, wherein the lower jaw of the end effector is configured to selectively receive a cartridge assembly, wherein the cartridge assembly includes:
- a cartridge body defining a longitudinally extending knife slot;
- a plurality of staples disposed in individual staple retaining slots formed in the cartridge body, wherein the staple retaining slots are arranged in multiple longitudinally extending rows disposed on opposed lateral sides of the knife slot;
- an actuation sled slidably supported in the cartridge body and being configured to expel at least a portion of the plurality of staples from the cartridge body upon a distal movement of the actuation sled from a proximal-most position; and
- a knife sled slidably supported in the cartridge body at a location proximal of the actuation sled, wherein the knife sled includes a knife blade extending into the knife slot;
- wherein the drive beam engages the knife sled and the actuation sled when the cartridge assembly is disposed in the lower jaw and when the drive beam is advanced.

8. The electromechanical surgical system according to claim 7, wherein the actuation sled of the cartridge assembly remains in a distally advanced position following any retraction of the drive beam.

9. The electromechanical surgical system according to claim 7, wherein the knife sled of the cartridge assembly includes a lock-out spring extending therefrom, wherein the lock-out spring of the knife sled engages a lock-out notch defined in the cartridge body to inhibit advancement of the knife sled.

10. The electromechanical surgical system according to claim 9, wherein, when the actuation sled and the knife sled are in a proximal-most position, the actuation sled blocks engagement of the lock-out spring of the knife sled with the lock-out notch of the cartridge body.

11. The electromechanical surgical system according to claim 10, wherein the knife sled of the cartridge assembly is retracted upon any retraction of the drive beam.

12. The electromechanical surgical system according to claim 11, wherein the drive beam includes a lock clip extending therefrom, wherein the lock clip of the drive beam engages the knife sled upon any distal advancement of the drive beam such that the knife sled retracts upon a retraction of the drive beam.

13. The electromechanical surgical system according to claim 12, wherein the at least one rotation receiving member of the end effector includes a drive screw rotatably supported in the lower jaw, wherein the drive beam is threadably supported on the drive screw, whereby rotation of the drive screw results in axial translation of the drive beam.

14. The electromechanical surgical system according to claim 5, wherein the at least one force transmitting assembly of the shaft assembly includes a first gear train system interconnecting the at least one rotatable drive member of the surgical instrument and the at least one rotation receiving member of the end effector, wherein the first gear train system varies at least one of:
- a rate of rotation between the at least one rotatable drive member of the surgical instrument and the at least one rotation receiving member of the end effector; and
- an axis of rotation between the at least one rotatable drive member of the surgical instrument and the at least one rotation receiving member of the end effector.

15. The electromechanical surgical system according to claim 14, wherein the at least one rotation receiving member of the end effector includes a drive screw rotatably supported in the lower jaw, wherein the drive beam is threadably supported on the drive screw, whereby rotation of the drive screw results in axial translation of the drive beam.

16. The electromechanical surgical system according to claim 14, wherein the shaft assembly includes an articulating neck assembly, and wherein the first gear train system is disposed proximal of the articulating neck assembly.

17. The electromechanical surgical system according to claim 16, wherein the shaft assembly includes a neck housing disposed distal of the articulating neck assembly, wherein the distal neck housing supports a neck first gear train of the at least one force transmitting assembly, wherein the neck first gear train interconnects an output of the first gear train system with the at least one rotation receiving member of the end effector, wherein the neck first gear train varies at least one of:
- a rate of rotation between the output of the first gear train system and the at least one rotation receiving member of the end effector; and
- an axis of rotation between the output of the first gear train system and the at least one rotation receiving member of the end effector.

18. The electromechanical surgical system according to claim 17, wherein the at least one rotation receiving member of the end effector includes a drive screw rotatably supported in the lower jaw, wherein the drive beam is threadably supported on the drive screw, whereby rotation of the drive screw results in axial translation of the drive beam.

19. The electromechanical surgical system according to claim 16, wherein the at least one force transmitting assembly of the shaft assembly includes a second gear train system interconnecting another of the at least one rotatable drive member of the surgical instrument and a rotation hub rotatably supported at a distal end of the neck housing, wherein the second gear train system varies at least one of:
- a rate of rotation between the another at least one rotatable drive member of the surgical instrument and the rotation hub of the shaft assembly; and
- an axis of rotation between the another at least one rotatable drive member of the surgical instrument and the rotation hub of the shaft assembly.

20. The electromechanical surgical system according to claim 14, wherein the shaft assembly further includes:
- an articulating neck assembly supported at a distal end of the outer tube;
- a distal neck housing supported at a distal end of the articulating neck assembly, and
- first and second diametrically opposed articulation cables extending at least partially along the neck assembly, wherein each articulation cable includes a distal end anchored to the distal neck housing, and a proximal end extending into the outer tube, the proximal end of each articulation cable being secured to a respective first and second rack, each rack being operatively connected to one another by a spur gear,
- wherein axial displacement of the first rack in a first direction results in:
  - axial displacement of the respective first articulation cable in the first direction;
  - articulation of the neck assembly in a first off-axis direction; and
  - axial displacement of the second articulation cable in a direction opposite to the first direction.

21. The electromechanical surgical system according to claim 20, wherein the shaft assembly further includes:
- a threaded rod extending proximally from the first rack; and
- a threaded shaft threadably connected to the threaded rod extending from the first rack, the threaded shaft being connected to another at least one drive member of the surgical instrument,
- wherein rotation of the another at least one drive member of the surgical instrument imparts rotation to the threaded shaft and, in turn, axial displacement of the threaded rod and first rack.

22. The electromechanical surgical system according to claim 14, wherein the shaft assembly further includes:
- an articulating neck assembly supported at a distal end of the outer tube, the neck assembly defining a central axis and being articulatable in a first plane;
- a distal neck housing supported at a distal end of the articulating neck assembly,
- first and second diametrically opposed articulation cables extending at least partially along the neck assembly;
- a first drive cable extending at least partially along the neck assembly and defining a first drive axis spaced a radial distance from the central axis, the first drive axis being defined by a first drive plane extending orthogonal to the first plane; and
- a second drive cable extending at least partially along the neck assembly and defining a second drive axis spaced a radial distance from the central axis, the second drive axis being defined by a second drive plane extending orthogonal to the first plane;
- wherein the first drive cable and the second drive cable are diametrically opposed to one another.

23. The electromechanical surgical system according to claim 1, wherein the end effector includes:
- an upper jaw and a lower jaw, at least one of the upper jaw and the lower jaw being movable in relation to the other of the upper jaw and the lower jaw.

24. The electromechanical surgical system according to claim 23, further comprising:
- at least one surgical buttress releasably secured to a tissue contacting surface of at least one of the upper jaw and the lower jaw.

25. The electromechanical surgical system according to claim 23, further comprising a drive beam translatable through at least one of the upper jaw and the lower jaw to move the lower jaw relative to the upper jaw.

26. The electromechanical surgical system according to claim 23, wherein the at least one rotation receiving member of the end effector includes a drive screw rotatably supported in the lower jaw, wherein the drive beam is threadably supported on the drive screw, whereby rotation of the drive screw results in axial translation of the drive beam.

* * * * *